(12) United States Patent
Chi et al.

(10) Patent No.: US 12,030,937 B2
(45) Date of Patent: Jul. 9, 2024

(54) ANTI-IDIOTYPIC ANTIBODIES AGAINST ANTI-GPRC5D ANTIBODIES

(71) Applicant: Janssen Biotech, Inc., Horsham, PA (US)

(72) Inventors: Ellen Chi, Del Mar, CA (US); Wilson Edwards, Cardiff by the Sea, CA (US); Matt Husovsky, Ramona, CA (US); Ann Lacombe, San Diego, CA (US); Christian Martinez, San Diego, CA (US); H. Mimi Zhou, San Diego, CA (US); John T. Lee, Ambler, PA (US)

(73) Assignee: Janssen Biotech, Inc., Horsham, PA (US)

( * ) Notice: Subject to any disclaimer, the term of this patent is extended or adjusted under 35 U.S.C. 154(b) by 182 days.

(21) Appl. No.: 17/376,874

(22) Filed: Jul. 15, 2021

(65) Prior Publication Data
US 2022/0064284 A1 Mar. 3, 2022

Related U.S. Application Data

(60) Provisional application No. 63/053,286, filed on Jul. 17, 2020.

(51) Int. Cl.
C07K 16/28 (2006.01)
G01N 33/50 (2006.01)

(52) U.S. Cl.
CPC ......... C07K 16/28 (2013.01); G01N 33/5005 (2013.01); C07K 2317/21 (2013.01); C07K 2317/24 (2013.01); C07K 2317/565 (2013.01); C07K 2317/567 (2013.01); G01N 2333/705 (2013.01)

(58) Field of Classification Search
None
See application file for complete search history.

(56) References Cited

U.S. PATENT DOCUMENTS

| | | | |
|---|---|---|---|
| 5,545,806 | A | 8/1996 | Lonberg et al. |
| 5,569,825 | A | 10/1996 | Lonberg et al. |
| 5,714,352 | A | 2/1998 | Jakobovits |
| 6,265,150 | B1 | 7/2001 | Terstappen et al. |
| 2002/0197266 | A1 | 2/2002 | Debinski |
| 2007/0004909 | A1 | 1/2007 | Johnson et al. |

(Continued)

FOREIGN PATENT DOCUMENTS

| | | |
|---|---|---|
| WO | WO2009/085462 | 7/2009 |
| WO | WO2018/017786 | 1/2018 |

(Continued)

OTHER PUBLICATIONS

Cheadle, E.J., et al., "Chimeric Antigen Receptors for T-Cell Based Therapy", (2012), Methods in Molecular Biology, vol. 907, pp. 645-666.

(Continued)

Primary Examiner — Aurora M Fontainhas

(57) ABSTRACT

In certain aspects, the disclosure relates to anti-idiotype antibodies and antigen-binding portions thereof that specifically bind a GP5B83 containing protein, e.g., an antibody or antigen-binding portions thereof. In some aspects, the anti-idiotype antibodies and antigen-binding portions of the present disclosure can be used in methods to detect and quantify cells expressing chimeric antigen receptors that include GP5B83.

30 Claims, 5 Drawing Sheets

Specification includes a Sequence Listing.

(56) References Cited

U.S. PATENT DOCUMENTS

2009/0060910 A1 3/2009 Johnson et al.
2010/0021477 A1 1/2010 Tsui et al.

FOREIGN PATENT DOCUMENTS

WO  WO2020/148677  7/2020
WO  WO2021/113780  6/2021

OTHER PUBLICATIONS

Wu, T.T., et al., "An Analysis of the Sequences of the Variable Regions of Bence Jones Proteins and Myeloma Light Chains and Their Implications for Anti-body Complementarity", (1970), J. Exp. Med. 132, pp. 211-250.

Chothia, C., et al., "Canonical Structures for the Hypervariable Regions of Immunoglobulins", (1987), J. Mol. Biol., vol. 196, pp. 901-917.

Lefranc, M.P., et al., "IMGT unique numbering for immunoglobulin and T cell receptor variable domains and Ig superfamily V-like domains", (2003), Development and Comparative Immunology, vol. 27, pp. 55-77.

Knappik, A., et al., "Fully Synthetic Human Combinatorial Antibody Libraries (HuCAL) Based on Modular Consensus Frameworks and CDRs Randomized with Trinucleotides", J. Mol. Biol., (2000), vol. 296, pp. 57-86.

Shi, L., et al., "De Novo Selection of High-Affinity Antibodies from Synthetic Fab Libraries Displayed on Phage as pIX Fusion Proteins", J. Mol. Biol., (2010), vol. 397, pp. 385-396.

Kohler, G., et al., "Derivation of specific antibody-producing tissue culture and tumor lines by cell fusion", (1976), Eur. J. Immunol., vol. 6, pp. 511-519.

Haskard, D.O., et al., The Production of Human Monoclonal Autoantibodies from Patients with Rheumatoid Arthritis by the EBV-Hybridoma Technique, (1984), Journal of Immunological Methods, vol. 74, pp. 361-367.

Roder, J.C., et al., "The EBV-Hybridoma Technique", (1986), The Methods of Enzymology, vol. 121, pp. 140-167.

Huse, W.D., et al., "Generation of a Large Combinatorial Library of the Immunoglobulin Repertoire in Phage Lambda", (1989), Science, vol. 246, pp. 1275-1281.

Tatusova, T.A., "Blast 2 Sequences, a new tool for comparing protein and nucleotide sequences", (1999), FEMS Microbiology Letters, vol. 174, pp. 247-250.

International Search Report from PCT/IB2021/056418 dated Nov. 4, 2021.

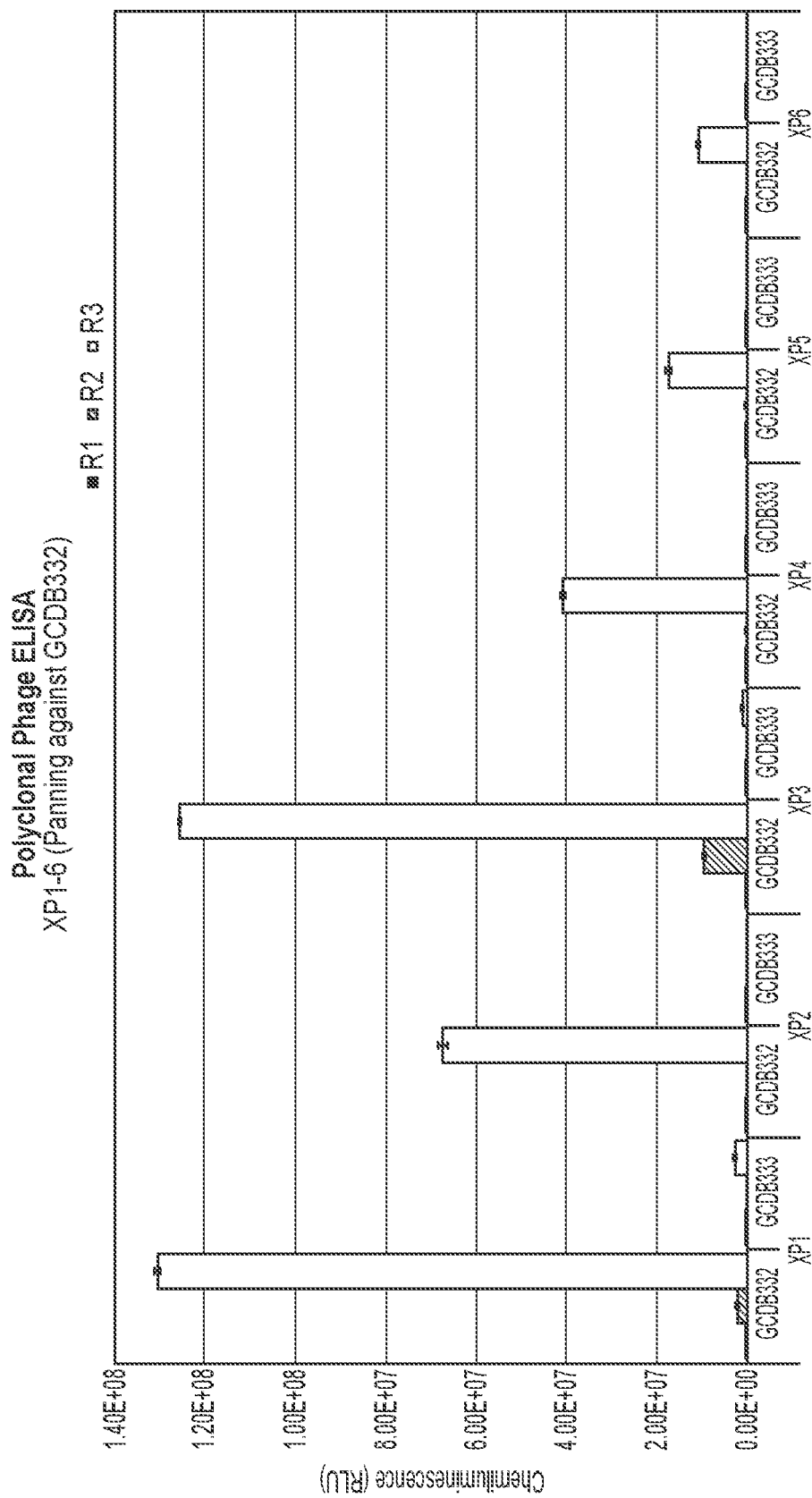

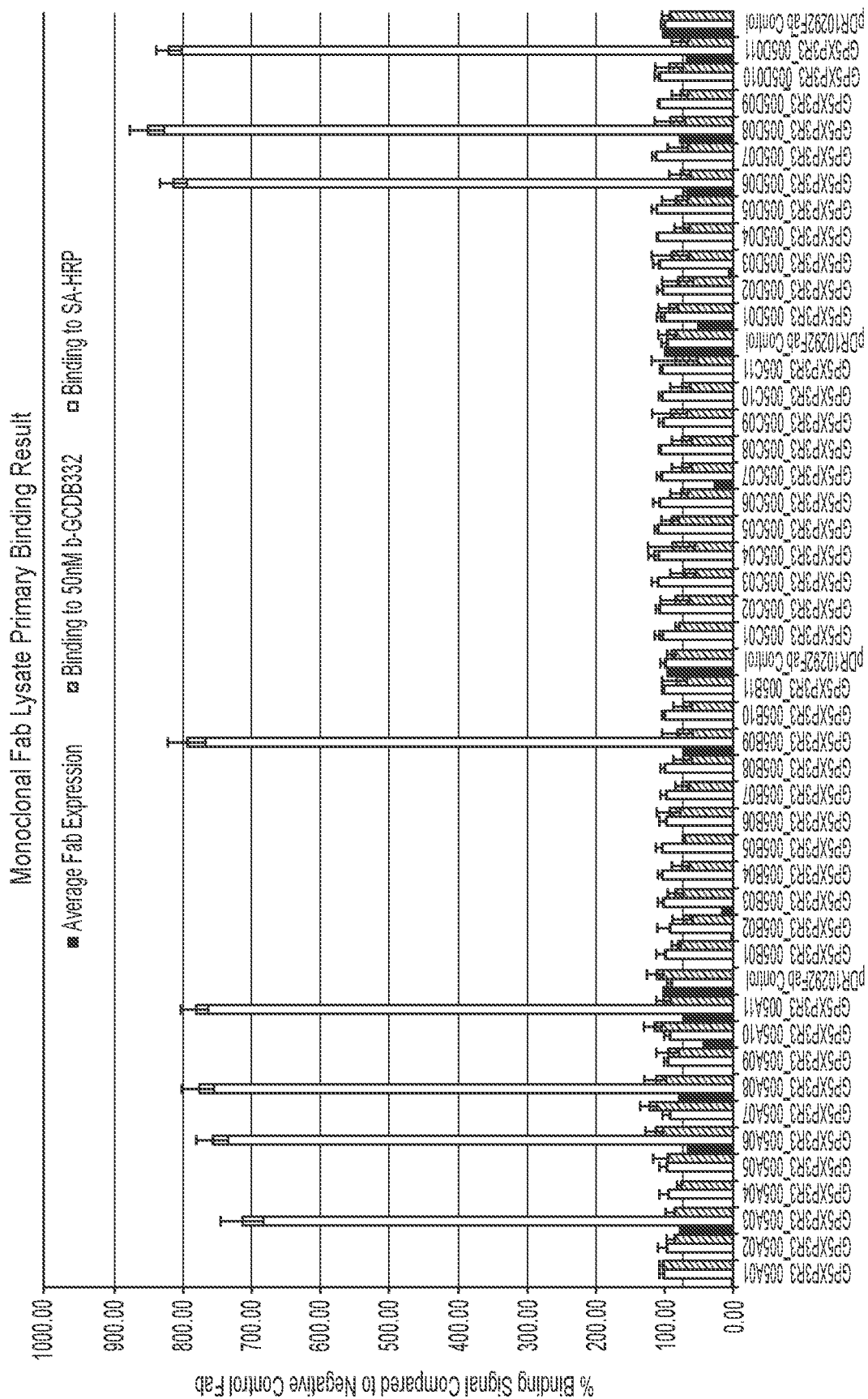

SEQUENCE LISTING

<160> NUMBER OF SEQ ID NOS: 48

<210> SEQ ID NO 1
<211> LENGTH: 25
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe
            20                  25

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Ser Phe Thr Ser Tyr
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Ser Phe Thr Ser Tyr Trp Ile Gly
1               5                   10

<210> SEQ ID NO 6
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 6

Ser Tyr Trp Ile Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Ser Tyr Trp Ile Gly
1               5

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ile Gly Trp Val Arg Gln Met Pro Gly Lys Gly Leu Glu Trp Met
1               5                   10                  15

Gly Ile Ile

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Val Arg Gln Met Pro Gly Lys Gly Leu Glu Trp Met Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Val Arg Gln Met Pro Gly Lys Gly Leu Glu
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Tyr Pro Gly Asp Ser Asp
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Ile Tyr Pro Gly Asp Ser Asp Thr Arg
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Ile Tyr Pro Gly Asp Ser Asp Thr Arg Tyr Ser Pro Ser Phe Gln
1               5                   10                  15

Gly

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Met Gly Ile Ile Tyr Pro Gly Asp Ser Asp Thr Arg
1               5                   10

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Thr Arg Tyr Ser Pro Ser Phe Gln Gly Gln Val Thr Ile Ser Ala Asp
1               5                   10                  15

Lys Ser Ile Ser Thr Ala Tyr Leu Gln Trp Ser Ser Leu Lys Ala Ser
            20                  25                  30

Asp Thr Ala Met Tyr Tyr Cys Ala Arg
        35                  40

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Tyr Ser Pro Ser Phe Gln Gly Gln Val Thr Ile Ser Ala Asp Lys Ser

-continued

```
                1               5                  10                  15
Ile Ser Thr Ala Tyr Leu Gln Trp Ser Ser Leu Lys Ala Ser Asp Thr
                20                  25                  30

Ala Met Tyr Tyr Cys Ala Arg
            35

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Thr Ile Ser Ala Asp Lys Ser Ile Ser Thr Ala Tyr Leu Gln
1               5                  10                  15

Trp Ser Ser Leu Lys Ala Ser Asp Thr Ala Met Tyr Tyr Cys Ala Arg
                20                  25                  30

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Tyr Ser Pro Ser Phe Gln Gly Gln Val Thr Ile Ser Ala Asp Lys Ser
1               5                  10                  15

Ile Ser Thr Ala Tyr Leu Gln Trp Ser Ser Leu Lys Ala Ser Asp Thr
                20                  25                  30

Ala Met Tyr Tyr Cys
            35

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Trp Asp Tyr Gly Thr Gly Glu Phe Asp Tyr
1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Gly Trp Asp Tyr Gly Thr Gly Glu Phe Asp
1               5                  10

<210> SEQ ID NO 21
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 21

Trp Gly Gln Gly Thr Leu Val Thr Val Ser Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Trp Gly Gln Gly Thr Leu Val Thr Val Ser Ser
1               5                   10

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile
            20                  25

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Gln Ser Ile Gly Asn Trp Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Gly Asn Trp Leu Asn Trp Tyr
1               5

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Tyr Gln Gln Lys Pro Gly Lys Ala Pro Lys Leu Leu Ile Tyr
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gln Lys Pro Gly Lys Ala Pro Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Ala Ser Ser Leu Gln Ser
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Leu Ile Tyr Tyr Ala Ser Ser Leu Gln
1               5                   10

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30
```

```
<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Gly Val Pro Ser Arg Phe Ser Gly Ser Gly Ser Gly Thr Asp Phe
1               5                   10                  15

Thr Leu Thr Ile Ser Ser Leu Gln Pro Glu Asp Phe Ala Val Tyr Tyr
            20                  25                  30

Cys

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Ser Leu Ser Phe Pro Ile Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Ser Leu Ser Phe Pro Ile
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gly Gln Gly Thr Lys Val Glu Ile Lys
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Gly Gln Gly Thr Lys Val Glu Ile Lys
1               5                   10

<210> SEQ ID NO 37
<211> LENGTH: 450
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 37

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Trp Asp Tyr Gly Thr Gly Glu Phe Asp Tyr Trp Gly Gln
            100                 105                 110

Gly Thr Leu Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
```

```
                385           390           395           400
Leu Asp Ser Asp Gly Ser Tyr Phe Met Tyr Ser Lys Leu Arg Val Glu
                    405               410              415

Lys Lys Asn Trp Val Glu Arg Asn Ser Tyr Ser Cys Ser Val Val His
                420              425              430

Glu Gly Leu His Asn His His Thr Thr Lys Ser Phe Ser Arg Thr Pro
            435              440              445

Gly Lys
    450
```

<210> SEQ ID NO 38
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
gaagtgcagc tggtgcagag cggcgcggaa gtgaaaaaac cgggcgaaag cctgaaaatt      60
agctgcaaag gcagcggcta tagctttacc agctattgga ttggttgggt gcgccagatg     120
ccgggcaaag gcctggaatg gatgggcatt atttatccgg gtgatagcga tacccgttat     180
agcccgagct ttcagggcca ggtgaccatt agcgcggata aaagcattag caccgcgtat     240
ctgcagtgga gcagcctgaa agcgagcgat accgcgatgt attattgcgc gcgcggctgg     300
gactatggta ccggcgagtt cgactattgg ggccagggca ccctggtgac cgtgagcagc     360
gccaaaacaa cagcaccaag tgtctatcca ctggcccctg tgtgtggaga tacaactggc     420
tcctcggtga ctctaggatg cctggtcaag ggttatttcc ctgagccagt gaccttgacc     480
tggaactctg gatccctgtc cagtggtgtg cacaccttcc cagctgtcct gcagtctgac     540
ctctacaccc tcagcagctc agtgactgta acctcgagca cctggcccag ccagtccatc     600
acctgcaatg tggcccaccc ggcaagcagc accaaggtgg acaagaaaat tgagcccaga     660
gggcccacaa tcaagccctg tcctccatgc aaatgcccag cacctaacct cttgggtgga     720
ccatccgtct tcatcttccc tccaaagatc aaggatgtac tcatgatctc cctgagcccc     780
atagtcacat gtgtggtggt ggatgtgagc gaggatgacc cagatgtcca gatcagctgg     840
tttgtgaaca acgtggaagt acacacagct cagacacaaa cccatagaga ggattacaac     900
agtactctcc gggtggtcag tgccctcccc atccagcacc aggactggat gagtggcaag     960
gagttcaaat gcaaggtcaa caacaaagac ctcccagcgc ccatcgagag aaccatctca    1020
aaacccaaag ggtcagtaag agctccacag gtatatgtct tgcctccacc agaagaagag    1080
atgactaaga aacaggtcac tctgacctgc atggtcacag acttcatgcc tgaagacatt    1140
tacgtggagt ggaccaacaa cgggaaaaca gagctaaact acaagaacac tgaaccagtc    1200
ctggactctg atggttctta cttcatgtac agcaagctga gagtgaaaaa gaagaactgg    1260
gtggaaagaa atagctactc ctgttcagtg gtccacgagg gtctgcacaa tcaccacacg    1320
actaagagct ctcccggac tccgggtaaa                                      1350
```

<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Asn Trp
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser Leu Ser Phe Pro Ile
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210
```

<210> SEQ ID NO 40
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
gaaattgtgc tgacccagag cccgggcacc ctgagcctga gcccgggcga acgcgcgacc      60
ctgagctgcc gcgcgagcca gagcatcggt aactggctga actggtatca gcagaaaccg     120
ggcaaagcgc cgaaactgct gatttattac gcgagcagcc tgcagagcgg cgtgccgagc     180
cgctttagcg gcagcggcag cggcaccgat tttaccctga ccattagcag cctgcagccg     240
gaagattttg cggtgtatta ttgccagcag tccctttcct ttccgattac atttggccag     300
ggcaccaaag tggaaattaa acgggctgat gctgcaccga ctgtgtccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gt                        642
```

```
<210> SEQ ID NO 41
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Ser
            20                  25                  30

Ser Tyr Trp Trp Gly Trp Arg Gln Pro Pro Gly Arg Gly Leu Glu
        35                  40                  45

Trp Ile Gly Thr Met Tyr Tyr Ser Gly Asn Ile Tyr Tyr Asn Pro Ser
    50                  55                  60

Leu Gln Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Val Gly Tyr Ser Tyr Gly Arg Arg Phe Trp Tyr Phe
            100                 105                 110

Asp Leu Trp Gly Arg Gly Thr Leu Val Thr Val Ser Ser
        115                 120                 125

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 43
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Leu Ser Ser
             20                  25                  30

Ser Tyr Trp Trp Gly Trp Thr Arg Gln Pro Pro Gly Arg Gly Leu Glu
         35                  40                  45

Trp Ile Gly Thr Met Tyr Tyr Ser Gly Asn Ile Tyr Tyr Asn Pro Ser
 50                  55                  60

Leu Gln Ser Arg Ala Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg His Val Gly Tyr Ser Tyr Gly Arg Arg Phe Trp Tyr Phe
            100                 105                 110

Asp Leu Trp Gly Arg Gly Thr Leu Val Thr Val Ser Ser Gly Gly Ser
            115                 120                 125

Glu Gly Lys Ser Ser Gly Ser Gly Ser Glu Ser Lys Ser Thr Gly Gly
            130                 135                 140

Ser Glu Ile Val Leu Thr Gln Ser Pro Ala Thr Leu Ser Leu Ser Pro
145                 150                 155                 160

Gly Glu Arg Ala Thr Leu Ser Cys Arg Ala Ser Gln Ser Val Ser Ser
                165                 170                 175

Tyr Leu Ala Trp Tyr Gln Gln Lys Pro Gly Gln Ala Pro Arg Leu Leu
            180                 185                 190

Ile Tyr Asp Ala Ser Asn Arg Ala Thr Gly Ile Pro Ala Arg Phe Ser
        195                 200                 205

Gly Ser Gly Ser Gly Thr Asp Phe Thr Leu Thr Ile Ser Ser Leu Glu
210                 215                 220

Pro Glu Asp Phe Ala Val Tyr Tyr Cys Gln Gln Arg Ser Asn Trp Pro
225                 230                 235                 240

Pro Thr Phe Gly Gln Gly Thr Lys Val Glu Ile Lys Thr Ser Thr Pro
            245                 250                 255

Ala Pro Arg Pro Pro Thr Pro Ala Pro Thr Ile Ala Ser Gln Pro Leu
        260                 265                 270

Ser Leu Arg Pro Glu Ala Cys Arg Pro Ala Ala Gly Gly Ala Val His
            275                 280                 285

Thr Arg Gly Leu Asp Phe Ala Cys Asp Ile Tyr Ile Trp Ala Pro Leu
290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
            325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
            355                 360                 365

Arg Ser Ala Asp Ala Pro Ala Tyr Lys Gln Gly Gln Asn Gln Leu Tyr
            370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430
```

```
Ala Tyr Ser Glu Ile Gly Met Lys Gly Glu Arg Arg Gly Lys Gly
                435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 44
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Gly Ser Gly Glu Gly
            100                 105                 110

Lys Ser Ser Gly Ser Gly Ser Glu Ser Lys Ser Thr Gly Gly Ser Gln
        115                 120                 125

Leu Gln Leu Gln Glu Ser Gly Pro Gly Leu Val Lys Pro Ser Glu Thr
    130                 135                 140

Leu Ser Leu Thr Cys Thr Val Ser Gly Gly Ser Leu Ser Ser Ser Ser
145                 150                 155                 160

Tyr Trp Trp Gly Trp Thr Arg Gln Pro Pro Gly Arg Gly Leu Glu Trp
                165                 170                 175

Ile Gly Thr Met Tyr Tyr Ser Gly Asn Ile Tyr Tyr Asn Pro Ser Leu
            180                 185                 190

Gln Ser Arg Ala Thr Ile Ser Val Asp Thr Ser Lys Asn Gln Phe Ser
        195                 200                 205

Leu Lys Leu Ser Ser Val Thr Ala Ala Asp Thr Ala Val Tyr Tyr Cys
    210                 215                 220

Ala Arg His Val Gly Tyr Ser Tyr Gly Arg Arg Phe Trp Tyr Phe Asp
225                 230                 235                 240

Leu Trp Gly Arg Gly Thr Leu Val Thr Val Ser Ser Thr Ser Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320
```

```
Cys Lys Arg Gly Arg Lys Lys Leu Leu Tyr Ile Phe Lys Gln Pro Phe
                325                 330                 335

Met Arg Pro Val Gln Thr Thr Gln Glu Asp Gly Cys Ser Cys Arg
            340                 345                 350

Phe Pro Glu Glu Glu Glu Gly Gly Cys Glu Leu Arg Val Lys Phe Ser
                355                 360                 365

Arg Ser Ala Asp Ala Pro Ala Tyr Lys Gln Gly Gln Asn Gln Leu Tyr
            370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
            435                 440                 445

His Asp Gly Leu Tyr Gln Gly Leu Ser Thr Ala Thr Lys Asp Thr Tyr
        450                 455                 460

Asp Ala Leu His Met Gln Ala Leu Pro Pro Arg
465                 470                 475

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Trp Asp Tyr Gly Thr Gly Glu Phe Asp Tyr Trp Gly Gln
            100                 105                 110

Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Ile Gly Asn Trp
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser Leu Ser Phe Pro Ile
                85                  90                  95

Thr Phe Gly Gln Gly Thr Lys Val Glu Ile Lys
                100                 105

<210> SEQ ID NO 47
<211> LENGTH: 345
<212> TYPE: PRT
<213> ORGANISM: Homo sapiens

<400> SEQUENCE: 47

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Ala Phe Leu Phe Leu Met
        35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
                100                 105                 110

Asn Leu Val Lys Leu Val Arg Gly Cys Val Ser Phe Ser Trp Thr Thr
            115                 120                 125

Ile Leu Cys Ile Ala Ile Gly Cys Ser Leu Leu Gln Ile Ile Ile Ala
        130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
                180                 185                 190

Cys Gly Pro Cys Glu Asn Trp Lys Gln His Gly Arg Leu Ile Phe Ile
            195                 200                 205

Thr Val Leu Phe Ser Ile Ile Trp Val Val Trp Ile Ser Met Leu
        210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255

Tyr Ile Val Pro Glu Leu Cys Ile Leu Tyr Arg Ser Cys Arg Gln Glu
                260                 265                 270

Cys Pro Leu Gln Gly Asn Ala Cys Pro Val Thr Ala Tyr Gln His Ser
```

-continued

```
                275                 280                 285
Phe Gln Val Glu Asn Gln Glu Leu Ser Arg Ala Arg Asp Ser Asp Gly
        290                 295                 300
Ala Glu Glu Asp Val Ala Leu Thr Ser Tyr Gly Thr Pro Ile Gln Pro
305                 310                 315                 320
Gln Thr Val Asp Pro Thr Gln Glu Cys Phe Ile Pro Gln Ala Lys Leu
                325                 330                 335
Ser Pro Gln Gln Asp Ala Gly Gly Val
            340                 345

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Ala Trp Val Trp Thr Leu Leu Phe Leu Met Ala Ala Ala Gln Ser
1               5                   10                  15

Ile Gln Ala
```

ANTI-IDIOTYPIC ANTIBODIES AGAINST ANTI-GPRC5D ANTIBODIES

CROSS-REFERENCE TO RELATED APPLICATIONS

This application claims the benefit of U.S. Provisional Application Ser. No. 63/053,286, filed 17 Jul. 2020. The entire content of the aforementioned application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 7, 2021, is named JB16352USNP1_SL.txt and is 36,022 bytes in size.

TECHNICAL FIELD

The invention relates to anti-idiotype antibodies and antigen-binding portions thereof that specifically bind a GP5B83 containing protein, e.g., an antibody or antigen-binding portions thereof. Methods to detect and quantify cells expressing chimeric antigen receptors that include GP5B83 are also provided.

BACKGROUND

Recent advances in the understanding of the delivery of genomic material and integration into a target's genome have great potential to transform the standard-of-care for a variety of diseases. T cell therapy utilizes isolated T cells that have been genetically modified to enhance their specificity for a specific tumor associated antigen. Genetic modification may involve the expression of a chimeric antigen receptor (CAR) or an exogenous T cell receptor to provide new antigen specificity onto the T cell. T cells expressing chimeric antigen receptors (CAR-T cells) can induce tumor immunoreactivity.

One particular CAR target of interest is G-protein coupled receptor family C group 5 member D (GPRC5D). GPRC5D has been identified as a potential target for immunotherapy of multiple myeloma, as well as potentially other cancers. Accordingly, there is a need for CAR-T cell therapies for treating cancer. There is also a need for anti-idiotype antibodies directed to such CARs in order to detect, purify, or select proteins and cells expressing the CAR.

SUMMARY OF THE INVENTION

The disclosure provides anti-idiotype antibodies and antigen-binding portions thereof that specifically bind a GP5B83 containing protein, e.g., an antibody or antigen-binding portions thereof. The disclosure also provides nucleic acids encoding the anti-idiotype antibodies and antigen-binding portions thereof, methods of producing the anti-idiotype antibodies and antigen-binding portions thereof, methods of detecting GP5B83 using the anti-idiotype antibodies and antigen-binding portions thereof and kits including the anti-idiotype antibodies and antigen-binding portions thereof.

In one aspect, the disclosure provides an anti-idiotype antibody or antigen-binding portion thereof that specifically binds an anti-GPRC5D antibody, such as a target antibody that comprises GP5B83. In some embodiments, the target antibody or antigen-binding portion comprises a VH domain with an amino acid sequence comprising SEQ ID NOs:41 and a VL domain with an amino acid sequence comprising SEQ ID NOs:42.

In other embodiments, the anti-idiotype antibody or antigen-binding portion is for use in detecting GP5B83 in a biologic sample comprising: (a) providing a biological sample; (b) contacting the biological sample with the anti-idiotype antibody or antigen-binding portion; and (c) detecting the anti-idiotype antibody or antigen-binding portion.

In another aspect, the disclosure provides an anti-idiotype antibody or antigen-binding portion that specifically binds GP5B83 comprising a heavy chain variable (VH) domain comprising a VH CDR1 having an amino acid sequence selected from the group consisting of SEQ ID NOs:4-7, a VH CDR2 having an amino acid sequence selected from the group consisting of SEQ ID NOs:11-14 and a VH CDR3 having an amino acid sequence selected from the group consisting of SEQ ID NOs:19-20, and further comprising a light chain variable (VL) domain comprising a VL CDR1 having an amino acid sequence selected from the group consisting of SEQ ID NOs:25-26, a VL CDR2 having an amino acid sequence selected from the group consisting of SEQ ID NOs:29-30 and a VL CDR3 having an amino acid sequence selected from the group consisting of SEQ ID NO:33-34.

In some embodiments, the anti-idiotype antibody or antigen-binding portion thereof comprises a VH domain that has an amino acid sequence having at least 90% sequence identity to SEQ ID NO:45 and the VL domain has an amino acid sequence having at least 90% sequence identity to SEQ ID NO:46. In some embodiments, the anti-idiotype antibody or antigen-binding portion thereof comprises a heavy chain comprising an amino acid sequence having at least 90% sequence identity to SEQ ID NO: 37 and further comprises a light chain comprising an amino acid sequence having at least 90% sequence identity to SEQ ID NO:39. In some embodiments, the anti-idiotype antibody or antigen-binding portion thereof comprises a VH domain that has an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO:45. In some embodiments, the anti-idiotype antibody or antigen-binding portion thereof comprises a VL domain that has an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO:46.

In some embodiments, the anti-idiotype antibody or antigen-binding portion thereof comprises a VH domain that has an amino acid sequence of SEQ ID NO:45 and a VL domain that has an amino acid sequence of SEQ ID NO:46. In some other embodiments, the anti-idiotype antibody or antigen-binding portion thereof comprises a heavy chain comprising an amino acid sequence of SEQ ID NO:37 and further comprises a light chain comprising an amino acid sequence of SEQ ID NO:39.

In some embodiments, the antigen-binding portion is selected from a Fab, F(ab')2, or scFv. In some embodiments, the antibody is a monoclonal antibody. In some embodiments, the antibody is a chimeric antibody. In some embodiments, the chimeric antibody comprises a murine IgG2a framework. In some other embodiments, the antibody is a fully human antibody. In some embodiments, the anti-idiotype antibody or antigen-binding portion thereof is specific to GP5B83, wherein GP5B83 is within the antigen-binding domain of the extracellular portion of a chimeric antigen receptor (CAR). In some embodiments, GP5B83 is an scFv and the anti-idiotype antibody or antigen-binding portion specifically binds an epitope in the scFv of the CAR. In some embodiments, GP5B83 specifically binds GPRC5D. In some embodiments, the antibody or antigen-binding portion does not cross-react to other GPRC5D antibodies or other GPRC5D binding CARs. In some embodiments, the CAR has an amino acid sequence selected from the group consisting of SEQ ID NOs: 43-44.

In some embodiments, the disclosure provides a nucleic acid encoding the heavy chain, the light chain, or both, of the anti-idiotype antibody or antigen-binding portion.

In another aspect, the disclosure provides a nucleic acid encoding the heavy chain, the light chain, or both, of an anti-idiotype antibody or an antigen-binding portion thereof that specifically binds GP5B83, wherein said nucleic acid comprises: the nucleotide sequence of SEQ ID NO: 38; the nucleotide sequence of SEQ ID NO: 40; or both. In another aspect, the disclosure provides a vector comprising the nucleic acid sequence. In some embodiments, the vector is an expression vector. In another aspect, the disclosure provides a host cell comprising the vector. In some embodiments, the host cell is a mammalian cell.

In another aspect, the disclosure provides a method of producing an anti-idiotype antibody or antigen-binding portion thereof that specifically binds GP5B83, said method comprising culturing a host cell under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture. In some embodiments, the host cell encodes a vector comprising a nucleic acid encoding the anti-idiotype antibody or antigen-binding portion thereof.

In another aspect, the disclosure provides a method for detecting GP5B83 in a biologic sample comprising: (a) providing a biological sample; (b) contacting the biological sample with the anti-idiotype antibody or antigen-binding portion; and (c) detecting the anti-idiotype antibody or antigen-binding portion.

In another aspect, the disclosure provides a method for detecting expression of a chimeric antigen receptor (CAR) comprising GP5B83 in a biologic sample comprising: (a) providing a biological sample; (b) contacting the biological sample with the anti-idiotype antibody or antigen-binding portion; and (c) detecting the anti-idiotype antibody or antigen-binding portion, and thereby detecting the expression of the CAR.

In some embodiments, the antibody comprises a detectable label. In some embodiments, the method further comprises further comprises contacting the anti-idiotype antibody or antigen-binding portion with a detectable label before detecting the anti-idiotype antibody or antigen-binding portion. In some embodiments, the biological sample is blood, serum or urine.

In some aspects, the disclosure provides a kit for detecting GP5B83 in a biologic sample comprising: (a) an anti-idiotype antibody or antigen-binding portion; and (b) instructions for detecting the anti-idiotype antibody or antigen-binding portion.

In other aspects, the disclosure provides a method of purifying GP5B83 from a sample comprising: (a) providing a biological sample comprising GP5B83; (b) contacting the biological sample with the anti-idiotype antibody or antigen-binding portion; and (c) capturing the anti-idiotype antibody or antigen-binding portion, and thereby purifying GP5B83.

In other aspects, the disclosure provides a method of selecting CAR-T cells from a cell population comprising: (a) providing a biological sample comprising CAR-T cells; (b) contacting the biological sample with an anti-idiotype antibody or antigen-binding portion; and (c) capturing the anti-idiotype antibody or antigen-binding portion, and thereby selecting CAR-T cells. In some embodiments, the anti-idiotype antibody or antigen-binding portion thereof is specific to GP5B83.

The disclosure contemplates all combinations of any of the foregoing aspects and embodiments, as well as combinations with any of the embodiments set forth in the detailed description and examples.

BRIEF DESCRIPTION OF THE DRAWINGS

For the purpose of illustrating the invention, there are depicted in the drawings certain embodiments of the disclosure. However, the disclosure is not limited to the precise arrangements and instrumentalities of the embodiments depicted in the drawings.

FIG. 1 shows a graphical representation of GCDB332 specific binding enrichment after round four panning detected with Polyclonal ELISA;

DETAILED DESCRIPTION OF THE INVENTION

Overview

Figure 2:
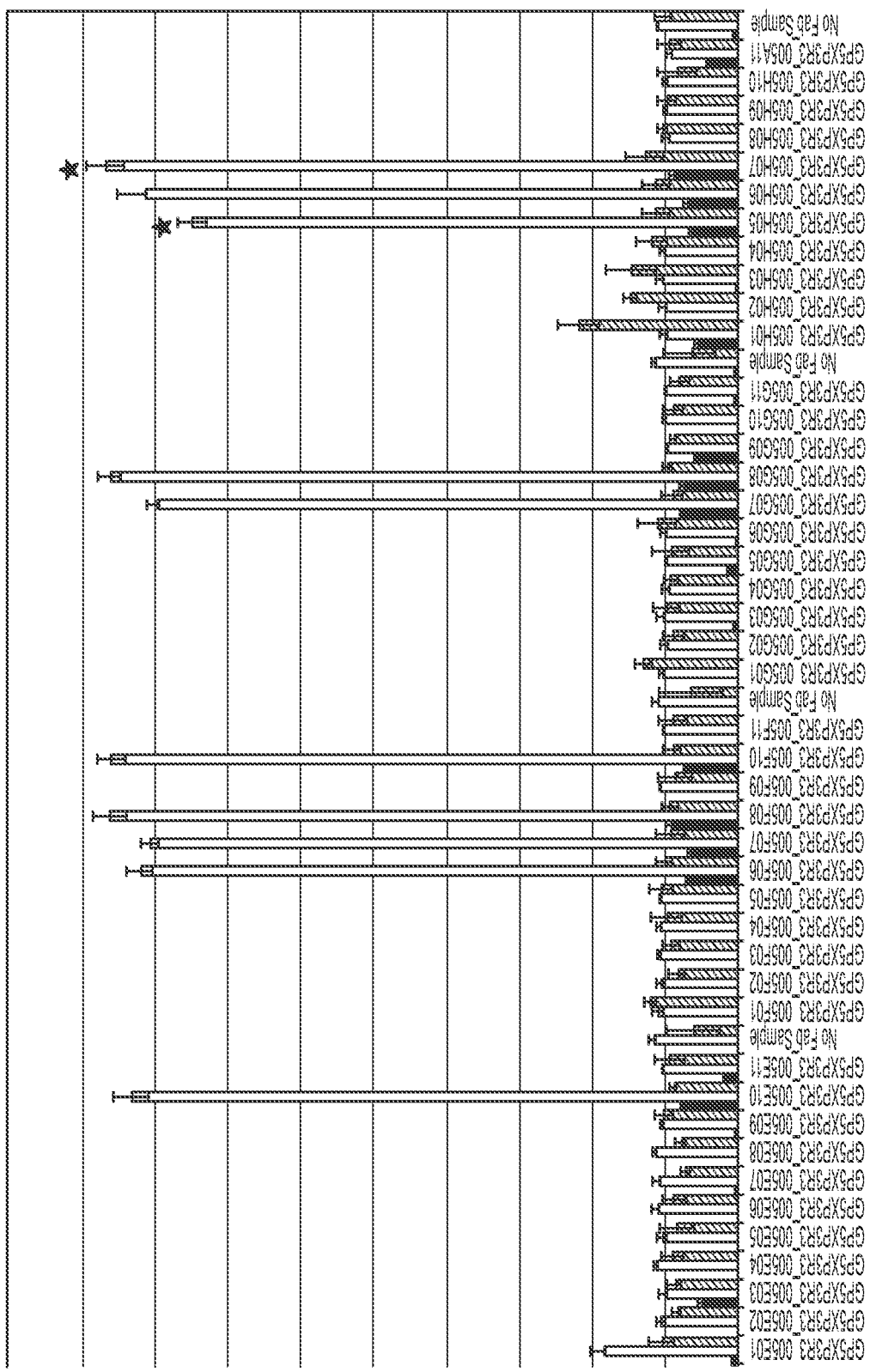
FIG. 2 shows a graphical representation of the results of monoclonal Fab binding screening from GCDB332 target binding assays compared with HRP-conjugated streptavidin counter screening reagent binding assays.

The disclosure provides anti-idiotype antibodies and antigen-binding portions thereof that specifically bind a GP5B83 containing protein, e.g., an antibody or antigen-binding portions thereof. The anti-idiotype antibodies and antigen-binding portions of the present disclosure can be used in methods to detect and quantify cells expressing CARs that include GP5B83. Such methods may allow a researcher to determine whether a given batch of in vitro generated CAR-T cells have expressed the desired CAR and thus whether the cells are therapeutically useful for targeting the desired proteins. In the present disclosure, the anti-idiotype antibodies and antigen-binding portions target GP5B83, which itself targets GPRC5D, a protein associated with cancers including multiple myeloma.

Definitions

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"Activation" or "stimulation" or "activated" or "stimulated" refers to induction of a change in the biologic state of a cell resulting in expression of activation markers, cytokine production, proliferation or mediating cytotoxicity of target cells. Cells may be activated by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

"Anti-idiotype antibody" or "anti-idiotypic antibody" refers to an antibody that specifically binds to the variable region of another antibody. In the case of GPRC5D, an anti-idiotype antibody specifically binds an anti-GPRC5D2 antibody.

"Antigen-binding portion," "antigen-binding fragment" or "antigen-binding domain" refers to a portion of the protein that binds an antigen. Antigen binding fragments may be synthetic, enzymatically obtainable or genetically engineered polypeptides and include portions of an immunoglobulin that bind an antigen, such as the VH, the VL, the VH and the VL, Fab, Fab', F(ab')2, Fd and Fv fragments, domain antibodies (dAb) consisting of one VH domain or one VL domain, shark variable IgNAR domains, camelized VH domains, VHH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3, alternative scaffolds that bind an antigen, and multispecific proteins comprising the antigen binding fragments. Antigen binding fragments (such as VH and VL) may be linked together via a synthetic linker to form various types of single antibody designs where the VH/VL domains may pair intramolecularly, or intermolecularly in those cases when the VH and VL domains are expressed by separate single chains, to form a monovalent antigen binding domain, such as single chain Fv (scFv) or diabody. Antigen binding fragments may also be conjugated to other antibodies, proteins, antigen binding fragments or alternative scaffolds which may be monospecific or multispecific to engineer bispecific and multispecific proteins.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"Full length antibody" is comprised of two heavy chains (HC) and two light chains (LC) inter-connected by disulfide bonds as well as multimers thereof (e.g. IgM). Each heavy chain is comprised of a heavy chain variable domain (VH) and a heavy chain constant domain, the heavy chain constant domain comprised of subdomains CH1, hinge, CH2 and CH3. Each light chain is comprised of a light chain variable domain (VL) and a light chain constant domain (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are antigen binding sites in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). The International ImMunoGeneTics (IMGT) database provides a standardized numbering and definition of antigen-binding sites. The correspondence between CDRs, HVs and IMGT delineations is described in Lefranc et al., Dev Comparat Immunol 27:55-77, 2003. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Modulate" refers to either enhanced or decreased ability of a test molecule to mediate an enhanced or a reduced response (i.e., downstream effect) when compared to the response mediated by a control or a vehicle.

"Natural killer cell" and "NK cell" are used interchangeably and synonymously herein. NK cell refers to a differentiated lymphocyte with a $CD16^+CD56^+$ and/or $CD57^+$ $TCR^-$ phenotype. NK cells are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"Specifically binds," "specific binding," "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant ($K_D$) of about $1 \times 10^{-7}$ M or less, for example about $5 \times 10^{-8}$ M or less, about $1 \times 10^{-8}$ M or less, about $1 \times 10^{-9}$ M or less, about $1 \times 10^{-10}$ M or less, about $1 \times 10^{-11}$ M or less, or about $1 \times 10^{-12}$ M, $1 \times 10^{-13}$ M, $1 \times 10^{-14}$ M, $1 \times 10^{-15}$ M or less, typically with the $K_D$ that is at least one hundred fold less than its $K_D$ for binding to a non-specific antigen (e.g., BSA, casein). In the context of the prostate neoantigens described here, "specific binding" refers to binding of the proteinaceous molecule to the prostate neoantigen without detectable binding to a wild-type protein the neoantigen is a variant of.

"Tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

The term "chimeric antigen receptor" or "CAR" as used herein is defined as a cell-surface receptor comprising an extracellular target-binding domain, a transmembrane domain and an intracellular signaling domain, all in a combination that is not naturally found together on a single protein. This particularly includes receptors wherein the extracellular domain and the intracellular signaling domain are not naturally found together on a single receptor protein. The chimeric antigen receptors of the present invention are intended primarily for use with lymphocyte such as T cells and natural killer (NK) cells.

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs", which refer to T cells that suppress an abnormal or excessive immune response and play a role in immune tolerance. Tregs are typically transcription factor Foxp3-positive CD4+ T cells and can also include transcription factor Foxp3-negative regulatory T cells that are IL-10-producing CD4+ T cells.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

The terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotype (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5a, JM109, and KCB, SURE® Competent Cells, and SOLO-PACK Gold Cells, can be used as host cells for vector replication and/or expression. Additionally, bacterial cells such as E. coli LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, effector function, persistence, and/or an increase in cancer cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid; these terms may also refer to the nucleic acid sequence including the portion coding for any amino acids added as an artifact of cloning, including any amino acids coded for by linkers.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

"GPRC5D" refers to G-protein coupled receptor family C group 5 member D, a known protein. The amino acid sequence of a full length human GPRC5D is shown in SEQ ID NO:47.

The term "GP5B83" refers to any antibody, antigen-binding portion thereof, or any other protein that contains variable regions derived from GP5B83-VH-N23S-N30S VH (SEQ ID 41) and GP5B83 VL (SEQ ID 42), including a CAR. "GP5B83" may used interchangeably with "GP5DB83." In certain embodiments, an anti-idiotype antibody of the disclosure specifically binds a protein comprising a VH domain as set forth in SEQ ID NO: 41 and/or a VL domain as set forth in SEQ ID NO: 42. In certain embodiments, an anti-idiotype antibody of the disclosure specifically binds a protein comprising the 3 CDRs of the VH domain set forth in SEQ ID NO: 41 and the 3 CDRs of the VL domain set forth in SEQ ID NO: 42.

The term "GCDB332" refers to a GP5B83-derived scFv-Fusion protein, specifically GP5B83-VH-N23S-N30S-LH-scFv.

The term "GP5B318" refers to a chimeric mAb with human VH/VL targeting GP5B83-derived scFv GCDB332 and murine IgG2a/k.

The terminology used herein is for the purpose of describing particular embodiments only and is not intended to be limiting. As used herein, the indefinite articles "a", "an" and "the" should be understood to include plural reference unless the context clearly indicates otherwise.

The disclosure further provides variants, e.g., functional variants, of the antibodies, nucleic acids, polypeptides, and proteins described herein. "Variant" refers to a polypeptide or a polynucleotide that differs from a reference polypeptide or a reference polynucleotide by one or more modifications for example, substitutions, insertions or deletions. The term "functional variant" as used herein refers to an antibody polypeptide, or protein having substantial or significant sequence identity or similarity to a parent antibody, polypeptide, or protein, which functional variant retains the biological activity of the antibody, polypeptide, or protein for which it is a variant. Functional variants encompass, e.g., those variants of the antibody, polypeptide, or protein described herein (the parent antibody, polypeptide, or protein) that retain the ability to recognize target cells to a similar extent, the same extent, or to a higher extent, as the parent antibody, polypeptide, or protein. In reference to the parent antibody, polypeptide, or protein, the functional variant can, for example, be at least about 30%, about 40%, about 50%, about 60%, about 75%, about 80%, about 85%, about 90%, about 91%, about 92%, about 93%, about 94%, about 95%, about 96%, about 97%, about 98%, about 99% or more identical in amino acid sequence to the parent antibody, polypeptide, or protein.

Herein, the structure of polypeptides is in places defined on the basis of % sequence identity with a recited reference sequence (with a given SEQ ID NO). In this context, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. Typically, the comparison window with correspond to the full length of the sequence being compared. For example, it is possible to use the BLAST program, "BLAST 2 sequences" (Tatusova et al, "Blast 2 sequences—a new tool for comparing protein and nucleotide sequences", FEMS Microbiol Lett. 174:247-250) the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program. Determining sequence identity of a query sequence to a reference sequence is within the ability of the skilled person and can be performed using commercially available analysis software such as BLAST™.

A functional variant can, for example, comprise the amino acid sequence of the parent antibody, polypeptide, or protein with at least one conservative amino acid substitution. In another embodiment, the functional variants can comprise the amino acid sequence of the parent antibody, polypeptide, or protein with at least one non-conservative amino acid substitution. In this case, the non-conservative amino acid substitution may not interfere with or inhibit the biological activity of the functional variant. The non-conservative amino acid substitution may enhance the biological activity of the functional variant such that the biological activity of the functional variant is increased as compared to the parent antibody, polypeptide, or protein.

Amino acid substitutions of the inventive antibodies may be conservative amino acid substitutions. Conservative amino acid substitutions are known in the art, and include amino acid substitutions in which one amino acid having certain physical and/or chemical properties is exchanged for another amino acid that has the same or similar chemical or physical properties. For example, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The antibodies, polypeptides, and proteins of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, α-(2-amino-2-norbornane)-carboxylic acid, α,γ-diaminobutyric acid, α,β-diaminopropionic acid, homophenylalanine, 4-chlorophenylalanine, 4-carboxyphenylalanine, β-phenyl serine β-hydroxyphenylalanine, phenylglycine, α-naphthylalanine, cyclohexylalanine, cyclohexylglycine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, indoline-2-carboxylic acid, 1,2,3,4-tetrahydroisoquinoline-3-carboxylic acid, aminomalonic acid, aminomalonic acid monoamide, and α-tert-butylglycine.

The antibodies, polypeptides, and proteins of embodiments of the invention (including functional portions and functional variants) can be subject to post-translational modifications. They can be glycosylated, esterified, N-acylated, amidated, carboxylated, phosphorylated, esterified, cyclized via, e.g., a disulfide bridge, or converted into an acid addition salt. In some embodiments, they are dimerized or polymerized, or conjugated.

The antibodies, polypeptides, and/or proteins of embodiments of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; and *Epitope Mapping*, ed. Westwood et al., Oxford University Press, Oxford, United Kingdom, 2001.

Also, polypeptides and proteins can be recombinantly produced using the nucleic acids described herein using standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. Further, some of the antibodies, polypeptides, and proteins of the invention (including functional portions and functional variants thereof) can be isolated and/or purified from a source, such as a plant, a bacterium, an insect, a mammal, etc. Methods of isolation and purification are known in the art. Alternatively, the antibodies, polypeptides, and/or proteins described herein (including functional portions and functional variants thereof) can be commercially synthesized. In this respect, the antibodies, polypeptides, and proteins can be synthetic, recombinant, isolated, and/or purified.

Methods and Uses of the Disclosure

The disclosure provides anti-idiotype antibodies and antigen-binding portions thereof that specifically bind a GP5B83 containing protein, e.g., an antibody or antigen-binding portions thereof. For example, the anti-idiotype antibodies may include amino acid sequences complementary to portions of a GP5B83 antibody to facilitate specific binding. The disclosure also provides nucleic acids encoding the anti-idiotype antibodies and antigen-binding portions thereof, methods of producing the anti-idiotype antibodies and antigen-binding portions thereof, methods of detecting GP5B83 using the anti-idiotype antibodies and antigen-binding portions thereof and kits including the anti-idiotype antibodies and antigen-binding portions thereof. For example, the anti-idiotype antibodies may be included in kits containing other reagents and used to determine whether a given biological sample includes GP5B83/GCDB332 antibodies or fragments thereof, for example, expressed on the surface of a T cell in a CAR.

Methods of testing antibodies for the ability to bind to any functional portion of GP5B83 are known in the art and include any antibody-antigen binding assay, such as, for example, radioimmunoassay (RIA), Western blot, enzyme-linked immunosorbent assay (ELISA), immunoprecipitation, and competitive inhibition assays.

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display can also be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

In one aspect, the disclosure provides an anti-idiotype antibody or antigen-binding portion thereof that specifically binds a target antibody or CAR that comprises GP5B83. For example, the anti-idiotype antibody or antigen-binding portion may specifically bind one or more of the domains of the fragment antigen-binding region (Fab), including the VH and VL. In some embodiments, the anti-idiotype antibody or antigen-binding portion comprises a VH domain with an amino acid sequence of SEQ ID NOs:45 and a VL domain with an amino acid sequence of SEQ ID NOs:46.

In other embodiments, the anti-idiotype antibody or antigen-binding portion is for use in detecting GP5B83 in a biologic sample comprising: (a) providing a biological sample; (b) contacting the biological sample with the anti-idiotype antibody or antigen-binding portion; and (c) detecting the anti-idiotype antibody or antigen-binding portion. For example, an anti-idiotype antibody may be added to any biologic sample, including: a tissue sample, a tumor sample, a cell or a fluid with other biological components, organisms, subunits of proteins/antigens, killed or inactivated whole cells or lysates. The anti-idiotype antibody may be contained in a solution containing pharmaceutically acceptable reagents, including but not limited to buffers, a stabilizer, and/or polymers. The anti-idiotype antibody may be contacted by pipetting and/or mixing with the biologic sample. Then anti-idiotype antibody may then specifically bind a GP5B83 containing protein, e.g., an antibody or antigen-binding portions thereof, in the biologic sample. As one example, whether an anti-idiotype antibody has bound to GP5B83 may be determined by washing unbound anti-idiotype antibody, leaving only complexed anti-idiotype antibody. Continuing with this example, the anti-idiotype antibody may include a fluorophore, which may be illuminated to give a signal proportional to the amount of GP5B83 in the biologic sample. Detection of a bound complex of anti-idiotype antibody to GP5B83 is described further below.

In another aspect, the disclosure provides an anti-idiotype antibody or antigen-binding portion that specifically binds an anti-GPRC5D2 antibody that comprises a heavy chain variable (VH) domain comprising a VH CDR1 having an amino acid sequence selected from the group consisting of SEQ ID NOs:4-7, a VH CDR2 having an amino acid sequence selected from the group consisting of SEQ ID NOs:11-14 and a VH CDR3 having an amino acid sequence selected from the group consisting of SEQ ID NOs:19-20, and further comprises a light chain variable (VL) domain comprising a VL CDR1 having an amino acid sequence selected from the group consisting of SEQ ID NOs:25-26, a VL CDR2 having an amino acid sequence selected from the group consisting of SEQ ID NOs:29-30 and a VL CDR3 having an amino acid sequence selected from the group consisting of SEQ ID NO:33-34. The six CDRs may be selected according to any known methods. The VH and VL CDRs determined according to Kabat, AbM, Chothia and contact methods are shown in Table 3.

In certain embodiments, the disclosure provides an anti-idiotype antibody or antigen-binding portion that specifically binds an anti-GPRC5D2 antibody that comprises a heavy chain variable (VH) domain comprising a VH CDR1 having an amino acid sequence of SEQ ID NO:4, a VH CDR2 having an amino acid sequence of SEQ ID NO:11 and a VH CDR3 having an amino acid sequence of SEQ ID NO:19, and further comprises a light chain variable (VL) domain comprising a VL CDR1 having an amino acid sequence of SEQ ID NO:25, a VL CDR2 having an amino acid sequence of SEQ ID NO:29 and a VL CDR3 having an amino acid sequence of SEQ ID NO:33.

In certain embodiments, the disclosure provides an anti-idiotype antibody or antigen-binding portion that specifically binds an anti-GPRC5D2 antibody that comprises a heavy chain variable (VH) domain comprising a VH CDR1 having an amino acid sequence of SEQ ID NO:5, a VH CDR2 having an amino acid sequence of SEQ ID NO:12 and a VH CDR3 having an amino acid sequence of SEQ ID NO:19, and further comprises a light chain variable (VL) domain comprising a VL CDR1 having an amino acid sequence of SEQ ID NO:25, a VL CDR2 having an amino acid sequence of SEQ ID NO:29 and a VL CDR3 having an amino acid sequence of SEQ ID NO:33.

In certain embodiments, the disclosure provides an anti-idiotype antibody or antigen-binding portion that specifically binds an anti-GPRC5D2 antibody that comprises a heavy chain variable (VH) domain comprising a VH CDR1 having an amino acid sequence of SEQ ID NO:6, a VH CDR2 having an amino acid sequence of SEQ ID NO:13 and a VH CDR3 having an amino acid sequence of SEQ ID NO:19, and further comprises a light chain variable (VL) domain comprising a VL CDR1 having an amino acid sequence of SEQ ID NO:25, a VL CDR2 having an amino acid sequence of SEQ ID NO:29 and a VL CDR3 having an amino acid sequence of SEQ ID NO:33.

In certain embodiments, the disclosure provides an anti-idiotype antibody or antigen-binding portion that specifically binds an anti-GPRC5D2 antibody that comprises a heavy chain variable (VH) domain comprising a VH CDR1 having an amino acid sequence of SEQ ID NO:7, a VH CDR2 having an amino acid sequence of SEQ ID NO:14 and a VH CDR3 having an amino acid sequence of SEQ ID NO:20, and further comprises a light chain variable (VL) domain comprising a VL CDR1 having an amino acid sequence of SEQ ID NO:26, a VL CDR2 having an amino acid sequence of SEQ ID NO:30 and a VL CDR3 having an amino acid sequence of SEQ ID NO:34.

In some embodiments, the anti-idiotype antibody or antigen-binding portion thereof that specifically binds an anti-GPRC5D2 antibody comprises a VH domain that has an amino acid sequence having at least 90% sequence identity to SEQ ID NO:45 and the VL domain has an amino acid sequence having at least 90% sequence identity to SEQ ID NO:46. In some embodiments, the anti-idiotype antibody or antigen-binding portion thereof that specifically binds an anti-GPRC5D2 antibody comprises a heavy chain comprising an amino acid sequence having at least 90% sequence identity to SEQ ID NO: 37 and further comprises a light chain comprising an amino acid sequence having at least 90% sequence identity to SEQ ID NO:39.

In some embodiments, the anti-idiotype antibody or antigen-binding portion thereof that specifically binds an anti-GPRC5D2 antibody comprises a VH domain that has an amino acid sequence of SEQ ID NO:45 and a VL domain that has an amino acid sequence of SEQ ID NO:46. In some other embodiments, the anti-idiotype antibody or antigen-binding portion thereof that specifically binds an anti-GPRC5D2 antibody comprises a heavy chain comprising an amino acid sequence of SEQ ID NO:37 and further comprises a light chain comprising an amino acid sequence of SEQ ID NO:39.

In some embodiments, the antigen-binding portion is selected from a Fab, F(ab')2, or scFv. In some embodiments, the antibody is a monoclonal antibody. In some embodiments, the antibody is a chimeric antibody. In some embodiments, the chimeric antibody comprises a murine IgG2a framework. In certain embodiments, the murine IgG2a framework may include a murine Ig heavy chain signal peptide from mix FVB/N, C57BL/6J comprising the sequence MAWVWTLLFLMAAAQSIQA (SEQ ID NO: 48).

In some other embodiments, the antibody is a fully human antibody. For example, the fully human antibody may be an IgG, IgM, IgA, IgE, or IgD. In some embodiments, the anti-idiotype antibody or antigen-binding portion thereof is specific to GP5B83, wherein GP5B83 is within the antigen-binding domain of the extracellular portion of a chimeric antigen receptor (CAR). For example, a GP5B83 encoding nucleic acid may be introduced in vitro into a T-cell, of which at least some portion then is expressed on the extracellular portion of a CAR. The anti-idiotype antibody may then specifically bind the extracellular portion of the CAR. In some embodiments, GP5B83 is an scFv and the anti-idiotype antibody or antigen-binding portion specifically binds an epitope in the scFv of the CAR. In some embodiments, GP5B83 specifically binds GPRC5D. In some embodiments, the antibody or antigen-binding portion does not cross-react to other GPRC5D antibodies or other GPRC5D binding CARs. For example, to prevent false positives in an assay for determining whether GP5B83 has been expressed on the extracellular portion of a CAR, the anti-idiotype antibody may be specific to GP5B83, and not have appreciable binding to its target GPRC5D or other GPRC5D targeting ligands that are not GP5B83. In some embodiments, the CAR has an amino acid sequence selected from the group consisting of SEQ ID NOs.:43-44.

In some embodiments, the disclosure provides a nucleic acid encoding the heavy chain, the light chain, or both, of the anti-idiotype antibody or antigen-binding portion. For example, the nucleic acid may be DNA, RNA, and any chemical modifications thereto (e.g., nucleoside modifications).

In another aspect, the disclosure provides a nucleic acid encoding the heavy chain, the light chain, or both, of an anti-idiotype antibody or an antigen-binding portion thereof that specifically binds GP5B83, wherein said nucleic acid comprises: the nucleotide sequence of SEQ ID NO: 38; the nucleotide sequence of SEQ ID NO: 40; or both. In another aspect, the disclosure provides a vector comprising the nucleic acid sequence. For example, the vector may be a self-replicating nucleic acid structure, or incorporated into the genome of a host cell into which it has been introduced. In some embodiments, the vector is an expression vector. In another aspect, the disclosure provides a host cell comprising the vector. In some embodiments, the host cell is a mammalian cell.

In another aspect, the disclosure provides a method of producing an anti-idiotype antibody or antigen-binding portion thereof that specifically binds GP5B83, said method comprising culturing a host cell under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture. For example, the anti-idiotype antibody may be produced by homogenous suspension culture in deep-tank stirred fermenters, perfusion-tank systems, airlift reactors, and continuous-culture systems. Anti-idiotype antibodies may be isolated from reaction and/or growth mixtures by physical or chemical separation procedures, including affinity separation using Protein A or G, size exclusion chromatography, and charge separations. In some embodiments, the host cell encodes a vector comprising a nucleic acid encoding the anti-idiotype antibody or antigen-binding portion thereof.

In another aspect, the disclosure provides a method for detecting GP5B83 in a biologic sample comprising: (a) providing a biological sample; (b) contacting the biological sample with the anti-idiotype antibody or antigen-binding portion; and (c) detecting the anti-idiotype antibody or antigen-binding portion. For example, the anti-idiotype antibody may bind GP5B83 expressed in the biological sample. The bound complex may be detected by any detection method, including both chemical and physical detection methods. For example, the detecting method may be used to identify the mere presence of the antibody of interest in a biological sample, or may be used to test whether the antibody of interest in a sample is present at a detectable level, or may be used to quantify the amount of the antibody of interest in a sample and further to compare the antibody levels from different samples. For example, the detecting method may be one or more of: immunoprecipitation, immunocytochemistry, immunoblotting, and immunosorbent assays. As a specific example, the immunsorbent assay may be an ELISA or ELISA-type assay that includes a bound anti-idiotype antibody or fragment thereof over which the biologic sample is washed.

In another aspect, the disclosure provides a method for detecting expression of a chimeric antigen receptor (CAR) comprising GP5B83 in a biologic sample comprising: (a) providing a biological sample; (b) contacting the biological sample with the anti-idiotype antibody or antigen-binding portion; and (c) detecting the anti-idiotype antibody or antigen-binding portion, and thereby detecting the expression of the CAR.

In some embodiments, the antibody comprises a detectable label. In some embodiments, the method further comprises further comprises contacting the anti-idiotype antibody or antigen-binding portion with a detectable label before detecting the anti-idiotype antibody or antigen-binding portion. For example, the detectable label may be any chemical tag or component that is either integral to, binds to, or otherwise complexes to the anti-idiotype antibody and emits or otherwise provides a unique identifiable signal. For example, the detectable label may be an isotope marker, colorimetric biosensor, photochromic compound, fluorescent label, fluorogenic label, or electrochemical sensor. As a specific example, the fluorescent label may be green fluorescent protein, yellow fluorescent protein, blue fluorescent protein, fluorescein, rhodamine, coumarin, cyanine, phycoerythrin, and derivatives thereof.

In some embodiments, the biological sample is blood, serum or urine. For example, the biological sample may be whole blood, serum, plasma, urine, feces, cerebrospinal fluid, ascites, and the like. In some embodiments, the biological sample is fresh biological material, such as biological material taken at a given time for the purpose of this analysis. The biological sample may also be biological material taken at another point during patient care for this or for other purposes, or using archived patient material. The biological sample may be freshly obtained or previously obtained, and where previously obtained may have been stored prior to use (e.g., at room temperature, refrigerated, or frozen).

In some aspects, the disclosure provides a kit for detecting GP5B83 in a biologic sample comprising: (a) an anti-idiotype antibody or antigen-binding portion; and (b) instructions for detecting the anti-idiotype antibody or antigen-binding portion. For example, the kit may include the anti-idiotype antibody or antigen binding portion as a solid powder, lyophilized powder, liquid solution or liquid components to mix to form a solution, or bound to a solid support. The kit may include additional reagents, including stabilizers, buffers, and other pharmaceutically acceptable excipients needed to facilitate using the kit in an assay of a biological sample. The kit may also include written instructions directing a user on how to perform the assay.

In other aspects, the disclosure provides a method of purifying GP5B83 from a sample comprising: (a) providing a biological sample comprising GP5B83; (b) contacting the biological sample with an anti-idiotype antibody or antigen-binding portion of the disclosure; and (c) capturing the anti-idiotype antibody or antigen-binding portion, including a CAR or other protein that contains GP5B83, and thereby purifying GP5B83. For example, any separation method, including physical and chemical methods, may be used to capture the anti-idiotype antibody. Specifically, the GP5B83 can be captured and isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the anti-idiotype antibody. In some embodiments, the anti-idiotype antibody is a fusion protein containing a domain which facilitates its purification. In certain embodiments, a purified GP5B83 composition is substantially isolated from proteins that do not contain GP5B83. In some embodiments, a purified GP5B83 composition is 100% pure, 99% pure, 98% pure, 97% pure, 96% pure, 95% pure, or 90% pure or greater.

In other aspects, the disclosure provides a method of selecting CAR-T cells from a cell population comprising: (a) providing a biological sample comprising CAR-T cells; (b) contacting the biological sample with an anti-idiotype antibody or antigen-binding portion; and (c) capturing the anti-idiotype antibody or antigen-binding portion, and thereby selecting CAR-T cells. In some embodiments, the anti-idiotype antibody or antigen-binding portion thereof is specific to GP5B83.

Embodiments

Particular non-limiting embodiments of the invention are set forth in the following numbered paragraphs.

1. An anti-idiotype antibody or antigen-binding portion thereof that specifically binds a target antibody that comprises GP5B83.

2. The anti-idiotype antibody or antigen-binding portion of paragraph 1, wherein the target antibody or antigen-binding portion thereof comprises a VH domain with an amino acid sequence of SEQ ID NO: 41 and a VL domain with an amino acid sequence of SEQ ID NO: 42.

3. An anti-idiotype antibody or an antigen-binding portion thereof that specifically binds GP5B83, wherein the anti-idiotype antibody or antigen-binding portion comprises a heavy chain variable (VH) domain comprising a VH CDR1 having an amino acid sequence selected from the group consisting of SEQ ID NOs:4-7, a VH CDR2 having an amino acid sequence selected from the group consisting of SEQ ID NOs:11-14 and a VH CDR3 having an amino acid sequence selected from the group consisting of SEQ ID NOs:19-20, and further comprises a light chain variable (VL) domain comprising a VL CDR1 having an amino acid sequence selected from the group consisting of SEQ ID NOs:25-26, a VL CDR2 having an amino acid sequence selected from the group consisting of SEQ ID NOs:29-30 and a VL CDR3 having an amino acid sequence selected from the group consisting of SEQ ID NO:33-34.

4. The anti-idiotype antibody or antigen-binding portion of any one of paragraphs 1-3, wherein the VH domain has an amino acid sequence having at least 90% sequence identity to SEQ ID NO:45 and the VL domain has an amino acid sequence having at least 90% sequence identity to SEQ ID NO:46.

5. The anti-idiotype antibody or antigen-binding portion of any one of paragraphs 1-3, wherein the anti-idiotype antibody or antigen-binding portion comprises a heavy chain comprising an amino acid sequence having at least 90% sequence identity to SEQ ID NO:37 and further comprises a light chain comprising an amino acid sequence having at least 90% sequence identity to SEQ ID NO:39.

6. The anti-idiotype antibody or antigen-binding portion of any one of paragraphs 1-3, wherein the VH domain has an amino acid sequence of SEQ ID NO:45 and the VL domain has an amino acid sequence of SEQ ID NO:46.

7. The anti-idiotype antibody or antigen-binding portion of any one of paragraphs 1-3, wherein the anti-idiotype antibody or antigen-binding portion comprises a heavy chain comprising an amino acid sequence of SEQ ID NO:37 and further comprises a light chain comprising an amino acid sequence of SEQ ID NO:39.

8. The anti-idiotype antibody or antigen-binding portion of any one of paragraphs 1-3, wherein the antigen binding portion is selected from a Fab, F(ab')2, or scFv.

9. The anti-idiotype antibody or antigen-binding portion of any one of paragraphs 1-3, wherein the antibody is a monoclonal antibody.

10. The anti-idiotype antibody or antigen-binding portion of any one of paragraphs 1-3, wherein the antibody is a chimeric antibody.

11. The anti-idiotype antibody or antigen-binding portion of paragraph 10, wherein the antibody comprises a murine IgG2a framework.

12. The anti-idiotype antibody or antigen-binding portion of any one of paragraphs 1-3, wherein the antibody is a fully human antibody.

13. A nucleic acid encoding the heavy chain, the light chain, or both, of the anti-idiotype antibody or antigen-binding portion of any one of paragraphs 1-3.

14. A nucleic acid encoding the heavy chain, the light chain, or both, of an anti-idiotype antibody or an antigen-binding portion thereof that specifically binds GP5B83, wherein said nucleic acid comprises:

a) the nucleotide sequence of SEQ ID NO: 38;

b) the nucleotide sequence of SEQ ID NO: 40;

c) both a) and b).

15. A vector comprising the nucleic acid of paragraphs 14.

16. The vector of paragraph 15, wherein the vector is an expression vector.

17. A host cell comprising the vector of paragraph 16.

18. The host cell of paragraph 17, wherein the cell is a mammalian cell.

19. A method of producing an anti-idiotype antibody or antigen-binding portion thereof that specifically binds GP5B83, said method comprising culturing the host cell of paragraph 17 under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture.

20. A method for detecting GP5B83 in a biologic sample comprising: (a) providing a biological sample; (b) contacting the biological sample with the anti-idiotype antibody or antigen-binding portion of any one of paragraphs 1-3; and (c) detecting the anti-idiotype antibody or antigen-binding portion.

21. A method for detecting expression of a chimeric antigen receptor (CAR) comprising GP5B83 in a biologic sample comprising: (a) providing a biological sample; (b) contacting the biological sample with the anti-idiotype antibody or antigen-binding portion of any one of paragraphs 1-3; and (c) detecting the anti-idiotype antibody or antigen-binding portion, and thereby detecting the expression of the CAR.

22. The method according to paragraph 20, wherein the antibody comprises a detectable label.

23. The method according to paragraph 20, wherein the method further comprises contacting the anti-idiotype antibody or antigen-binding portion with a detectable label before detecting the anti-idiotype antibody or antigen-binding portion.

24. The method according to paragraph 20, wherein the biological sample is blood, serum or urine.

25. The anti-idiotype antibody or antigen-binding portion of any one of paragraphs 1-3, wherein GP5B83 is within the antigen-binding domain of the extracellular portion of a chimeric antigen receptor (CAR).

26. The anti-idiotype antibody or antigen-binding portion of paragraph 25 wherein GP5B83 is an scFv and the anti-idiotype antibody or antigen-binding portion specifically binds an epitope in the scFv of the CAR.

27. The anti-idiotype antibody or antigen-binding portion of paragraph 25, wherein GP5B83 specifically binds GPRC5d.

28. The anti-idiotype antibody or antigen-binding portion of paragraph 25, wherein the antibody or antigen-binding portion does not cross-react to other GPRC5d antibodies or other GPRC5d binding CARs.

29. The anti-idiotype antibody or antigen-binding portion of paragraph 25, wherein the CAR has an amino acid sequence selected from the group consisting of SEQ ID NO: 43-44.

30. A kit for detecting GP5B83 in a biologic sample comprising: (a) the anti-idiotype antibody or antigen-binding portion of any one of paragraphs 1-3; and (b) instructions for detecting the anti-idiotype antibody or antigen-binding portion.

31. The anti-idiotype antibody or antigen-binding portion of any one of paragraphs 1-3, for use in detecting GP5B83 in a biologic sample comprising: (a) providing a biological sample; (b) contacting the biological sample with the anti-idiotype antibody or antigen-binding portion; and (c) detecting the anti-idiotype antibody or antigen-binding portion.

32. A method of purifying GP5B83 from a sample comprising: (a) providing a biological sample comprising GP5B83; (b) contacting the biological sample with the anti-idiotype antibody or antigen-binding portion of any one of paragraphs 1-3; and (c) capturing the anti-idiotype antibody or antigen-binding portion, and thereby purifying GP5B83.

33. A method of selecting CAR-T cells from a cell population comprising: (a) providing a biological sample comprising CAR-T cells; (b) contacting the biological sample with the anti-idiotype antibody or antigen-binding portion of any one of paragraphs 1-3; and (c) capturing the anti-idiotype antibody or antigen-binding portion, and thereby selecting CAR-T cells.

EXAMPLES

Example 1: Determination of GCDB332 Binding Fabs

GP5B83-derived scFv-Fusion protein GCDB332 binding Fabs were selected from two sets of de novo Fab-pIX phage display libraries as described in Shi et al., J Mol Biol 397:385-96, 2010; Int. Pat. Publ. No. WO2009/085462; U.S. Pat. Publ. No. US2010/0021477).

In the phage selections using purified recombinant antigens, biotinylated GCDB332 were used as "bait" to capture and immobilize the phage binders. After several selection rounds, a polyclonal phage ELISA using purified antigens was performed to detect the specific enrichment of individual panning experiments. The phage collected from those panning experiments which demonstrated enrichment for binders to GCDB332 were expressed in E. coli for primary screening. Monoclonal Fab lysates were prepared from the enriched Fab libraries were screened in ELISA for binding to GCDB332 but not to background control. The selected Fabs were sequenced to identify the unique Fab clones and isolate their V region genes. The unique Fab V regions were cloned into mammalian expression vectors to express chimeric mAbs with murine IgG2a/murine Kappa constant regions. The chimeric mAbs were evaluated for specific binding to the scFv expressed on SupT1 cells (GP5B83) which corresponds to the scFv in the GCDB332 scFv fusion protein, and binding kinetics were measured using SPR.

Phage panning Six individual panning experiments using individual V3.0 and V5.0 de novo Fab phage libraries were panned against biotinylated GCDB332 according to standard protocol (Cheadle, E. J. et al. Antibody Engineering. 907, 645-666 (2012). Briefly, the phage libraries and paramagnetic streptavidin (SA) beads were blocked in 50% Chemiblocker (Millipore cat #2170)/50% 1×TBST (Teknova cat #T0310) for one hour. Libraries were added to the SA beads to adsorb clones that bind non-specifically to the beads. SA-beads were discarded, and the pre-adsorbed library was added to biotinylated GCDB332. Binders were retrieved by addition of SA-beads to form a bead/antigen/phage complex, which was washed in 1×TBST. After the final wash, phage was rescued by infection of log phase TG1 E. coli cells (OD600 nm=0.4-0.6). The phage-infected TG1 cells was spread on three 150-mm LB/Agar plates containing 75 µg/ml carbenicillin and 1% glucose then grown overnight at 37° C. Phage was produced and subjected for additional panning. To increase selection pressure, the antigen concentration was reduced and the incubation times lengthen for each subsequent rounds: R1 100 nM, 1 hour; R2 10 nM 1 hour; R3 10 nM 16 hours.

Polyclonal Phage ELISA

Enrichment of binders was determined from each panning experiment by polyclonal phage ELISA. Briefly, 100 µl of 20 nM nonbiotinylated GCDB332 diluted in 1×TBS (Teknova cat #T9530) was captured on NA-coated plate (Thermo cat #15217). After an hour incubation at 37° C., the plate was washed 3 times in 300 µl 1×TBST. 300 µl of blocking buffer 50% Chemiblocker/50% 1×TBST was added to each well of the plate and incubated at room temperature for 1 hour. After blocking, the plate was washed 3 times with 300 µl of 1×TBST. 100 µL of polyclonal phage output from each panning rounds diluted 1/100 diluted in assay buffer, 10% Chemiblocker/90% TBST, were added to the ELISA plate and incubated at room temperature for 1 hour to allow the binding of Fab displayed on the phage particles to the immobilized GCDB332. Following the incubation, the plate was washed 3 times with 1×TBST. 100 µl of HRP-conjugated anti-M13 (pVIII) antibody (GE Healthcare cat #27942101) diluted 1:2500 in assay buffer was added to the plate and incubated at room temperature. After 1 hour incubation, the plate was washed 6 times with 300 µl of 1×TBST. 100 µL of prepared BM chemiluminescence ELISA Substrate (Roche cat #11582950001) was added to the plate. The chemiluminescence or relative light unit (RLU) was measured by Envision plate reader. As shown in FIG. 1, all six panning experiments showed GCDB332 specific binding enrichment after round 3 panning. GP5B318 came from XP3 panning experiments.

Fab Production

Plasmid DNA were isolated and purified from glycerol stocks of specific rounds of phage panning experiments that were identified to demonstrate enrichment of binders to GCDB332, and transformed into TG-1 *E. coli* cells and grown on LB/Agar plates overnight. The overnight cultures were used for (i) colony PCR and sequencing of the V-regions, and (ii) starting culture for Fab production. For Fab production, the overnight culture was diluted 10-100 fold in new media and grown for 5-6 hours at 37° C. Fab production was induced by the addition of fresh media containing IPTG and the cultures were grown overnight at 30° C. The cultures were spun down and the bacterial pellet was lysed using BugBuster™ (Millipore) to release the soluble Fab proteins. The cell lysate was spun down and the supernatant were used for Fab ELISA.

Primary Screening

The phage collected from the panning experiments which demonstrated enrichment for binders to GCDB332 were expressed in *E. coli* for primary screening. The soluble Fab proteins were captured onto plates by a polyclonal sheep anti human Fd (CH1) antibody (The Binding Site). After appropriate washing and blocking, biotinylated GCDB332 was added at 50 nM concentration. This biotinylated GCDB332 was detected by HRP-conjugated streptavidin and ELISA Pico Chemiluminescent Substrate (Thermo cat #37069), then read in a plate reader. Additionally, HRP-conjugated streptavidin was used for counter-screening. The Fab clones with binding signal to GCDB332 four times or higher than the negative control Fabs, and binding signal to streptavidin-HRP equal to or less than the negative control Fabs were selected and sequenced.

FIG. 2 shows the results of the primary screening. Monoclonal Fabs were screened in ELISA in binding to GCDB332. Clones with 4-fold binder signals over the background were selected and sequences. The two clones identified by a star are the ones that generated the VH and VL in GP5B318.

Example 2: Generation of Monoclonal Antibodies Against GP5B83 (GP5B318)

Fab Selection

The selected Fabs from the primary screening were sequenced to determine V region sequences and identify unique clones. The unique Fab V regions were cloned into mammalian expression vectors to express as chimeric mAbs with murine IgG2a/murine Kappa constant regions.

The variable regions of GP5B318 were identified through phage display using human Fab-pIX de novo libraries to soluble scFv-Fc fusion protein GCDB332. These V-regions did not undergo any affinity maturation. The DNA sequences were obtained from the de novo Fab library without any codon optimization.

Cloning of $V_H$ and $V_L$,

Two pcDNA3.1 derived mammalian expression vector (vDR000368 and vDR000961) were used to generate the single gene constructs encoding the heavy chain (HC) or light chain (LC) of the chimeric mAb. Each vector contains a human cytomegalovirus (hCMV) promoter to drive the expression of the HC and LC and both contain the ampicillin resistance gene (Amp(R)) to facilitate cloning. vDR000368 has unique HindIII and DraIII restriction enzyme sites for cloning and also a mouse IgG2a constant region; vDR000961 has unique HindIII and Tth111I restriction enzyme sites for cloning and also a mouse Kappa constant region.

A DNA fragment comprising the variable region of HC (VH) or LC (VL), was synthesized by IDT and ligated into HC vector vDR000368 and LC vector vDR000961. The HC synthetic fragment included a HindIII restriction enzyme site, Kozak sequence, DNA sequences encoding a signal peptide, the VH and part of the CH1, and a DraIII cloning site. The LC synthetic fragment included a HindIII restriction enzyme site, Kozak sequence, DNA sequences encoding a signal peptide, the VL, and part of the Kappa constant region, and a Tth111I restriction cloning site. The final HC construct is PBD000094819 and the final LC construct is PBD000094818. The two constructs were co-transfected in mammalian expression cell lines HEK293 Expi or CHO to make GP5B318.

Protein Expression

The HC construct PBD000094819 and the LC construct PBD000094818 were sequenced verified before transfection. HEK Expi293™ cells (Thermo cat #A14527) grown in Expi293™ Expression media (Thermo cat #A1435101). The cells are grown at 37° C. shaking at 125 RPM with 8% $CO_2$. The cells were transfected at $2.5 \times 10^6$ cells per ml using Expi293™ Expression Kit (Thermo cat #A14524). For each liter of cells transfected 1 mg of total DNA was diluted in 25 ml of Opti-MEM (Thermo cat #319850620) and 2.6 ml of Expi293™ reagent was dilute d in 25 ml of Opti-MEM and incubated for 5 minutes at room temperature. The diluted DNA and diluted Expi293 reagent were combined and incubated for 20 minutes at room temperature. The DNA complex was then added to the cell. The cells were placed in the shaking incubator overnight. The next day after transfection 5 ml of Enhancer 1 was diluted into 50 ml of Enhancer 2 and the total volume of the two Enhancers were added to the cells. The transfected cells were placed back into the incubator for 4 days until harvested. The cells were removed by centrifugation at 4,500 g for 35 minutes then filtered with a 0.2 µm filter prior to checking expression levels.

Expression was quantitated by Octet. Murine IgG2 (Sigma Cat #M9144) was used as the standard. Protein A biosensors were used. The samples and the standard were diluted with spent Expi293 media. The standard curve started at 100 µg/ml in a twofold dilution. The samples were diluted 1:10. The standard curve was a linear point curve. The calculations performed by Forte Biosystems software.

Example 3: Binding Assays for Anti-Idotypic Antibody GP 5B318

Binding Assay Using Soluble Proteins with Proteon

ProteOn XPR36 system (BioRad) was used to perform binding assays. ProteOn GLC chips (BioRad, Cat #176-5011) were coated with Anti-Mouse Fc antibody. Library Antibodies (Mouse IgG2a) diluted to 0.25 ug/ml to 1 ug/ml to reach approximately 100-200RL. Antigens (scFV Fc Fusions) are associated at 50 nM to 0.2 nM, 1:4 dilutions for 3 minutes. Dissociation for 30 mins. The results of the assay (Table 1 below) show picomolar affinity of GP5B318 with GP5B305. GP5B305 is a bi-specific antibody that includes HC1 N-Terminal CD3B376-Fab/C-Terminal BCMB516-LH-scFv* and HC2 N-Terminal GP5B83 N23T, N30S-LH-scFv*.

TABLE 1

Proteon binding results for GP5B318 to GP5B305.

| | Proteon Binding to GP5B305 | | |
|---|---|---|---|
| Protein AA Name | ka 1/Ms | kd 1/s | KDM |
| GP5B318 | >1.0E+07 | <2.9E−05 | <2.9E−12 |

Cell Binding Assay

ScFv transfected SupT1-GP5B680 HL, SupT1-GP5B680 LH or GP5B83 cells were cultured in RMPI 1640, 10% FBS, 1% Non-Essential Amino Acids, 1 mM Sodium Pyruvate, 2 mM L-glutamine, 10 mM HEPES, 0.1% bicarbonate. Cell culture media and supplements were ThermoFisher Scientific Gibco products. The mAbs were diluted to either 1.0 or 0.1 micrograms/mL in Stain Buffer (BSA) (BD Pharmingen cat #554657). ScFv expressing SupT1 cells were added to 384 well V bottom polypropylene plates (Greiner Bio-One #781280 or #781281) at 50,000 cells/well. Plates containing the cells were centrifuged at 450×g for 2 minutes and supernatants aspirated. The diluted mAb samples were added to the cell pellets, mixed, and incubate on ice for 1 hour. Plates containing the cells were centrifuged at 450×g for 2 minutes and supernatants aspirated. Anti-mouse IgG heavy and light chain-PE conjugated secondary detection antibody (JacksonImmunoResearch, cat #115-116-146) diluted 1:200 in Stain Buffer (BSA) was added to the cell pellets, mixed, and incubated on ice for 30 minutes. Plates containing the cells were centrifuged at 450×g for 2 minutes and supernatants aspirated and cell pellets were resuspended inStain Buffer (BSA), mixed, and analyzed on the LSR II flow cytometer with HTS autosampler (Beckton Dickenson), and data was analyzed using Flowjo software (Treestar) for mean fluorescence intensities of the gated live population. All liquid handling was performed on an Agilent Bravo system and aspiration of 384-well plates were handled on a BioTek 405 Select plate washer.

As shown in Table 2, GP5B318 showed specific binding to the GP5B83 expressing cell line, but not to the negative controls SupT1-GP5B680-HL and SupT1-GP5B680-LH.

TABLE 2

Cell binding results for GP5B318 to GP5B680 LH and HL GP5B680 cells, and to GP5B83 expressing cells

| Protein | Cell Binding 1 ug/ml | | | Cell Binding 0.1 ug/ml | | |
|---|---|---|---|---|---|---|
| AA Name | GP5B680 LH | GP5B680 HL | GP5B83 | GP5B680 LH | GP5B680 HL | GP5B83 |
| GP5B318 | 139 | 140 | 19895 | 116 | 103 | 21483 |

Example 4: Characterization of Detection Antibodies for GPRC5D CAR GP5B83-LH on CAR+ SupT1 Cells Antibodies to detect GPRC5D CAR (GP5DB83-HL) expressed on NK and T cells were identified from panels of proteins derived from Phage Display screening. As discussed in the preceding examples, the proteins were tested initially for binding to recombinant CAR protein and potential binders were scaled up. The proteins were purified and tested for dose dependent binding to SupT1 cells expressing GP5DB83-HL by flow cytometry. The binding was determined to be specific to CAR through competition binding experiments with Fc-GP5DB83-HL fusion proteins and through lack of binding to parental SupT1 cells. After selection of the best binder, the antibodies were directly conjugated to recombinant phycoerythrin ("PE") for use as CAR detection reagents. The antibodies were purified to a 1:1 PE:antibody ratio to enable receptor enumeration studies (number of CAR expressed on the cell surface).

Purification

Cell culture supernatant was loaded to a Mab Select column and eluted with low pH buffer such as 100 mM sodium acetate pH 3.0, subsequently buffer exchanged to 1×SSC, 8.5% sucrose pH 7.0 using a Sephadex G-25 column. Fractions containing protein were collected. Following purification, proteins underwent QC using SDS-PAGE, SEC-HPLC and LC-MS methods.

Phycoerythrin Labeling

1 µL of Modifier reagent was added to each 10 µL of antibody to be labeled and mixed gently. The antibody sample (with added Modifier reagent) was pipetted directly onto the lyophilized PE (Expedeon, Cat #703-0015), then resuspended gently and incubated for 1 hour in the dark at room temperature (20-25° C.). 1 µL of Quencher reagent was added for every 10 µL of antibody used and incubated for 30 minutes.

After labeling, PE-antibody conjugates were purified on a size-exclusion chromatogram column. Fractions were collected and analyzed on SEC-HPLC. Fractions that only contained one antibody with one PE were pooled together and concentrated if necessary. Final products were analyzed on SEC-HPLC.

Characterization of GPRC5D CAR (GP5DB83-HL) CAR Anti-Idotypic Antibody GP5B318

Figure 3:
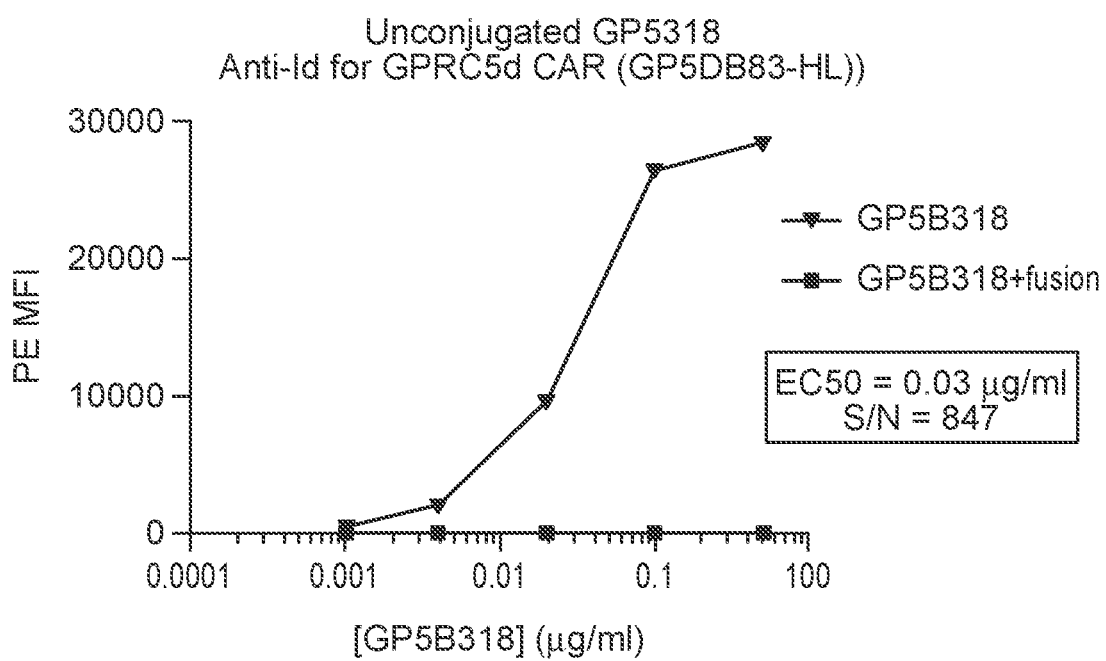
FIG. 3 shows a graphical representation of dose dependent binding of GP5B318 to GP5DB83-LH SupT1 cells.

SupT1 cells expressing GP5DB83-HL were compared to parental CAR− SupT1 cells. SupT1 cells expressing GP5DB83-HL and parental CAR− SupT1 cells were stained with near IR LIVE/DEAD fluorescent reactive dye on ice for 20 mins. After incubation, the cells were washed and resuspended in BSA stain buffer Cells (100,000 cells/well) were plated in a 96 well plate and incubated with increasing concentrations of GP5B318 for 30 minutes on ice with and without 10 μg/mL CAR-Fc Fusion protein, GP5B83_N24T_N315-HL-hu Fc-scFv (GP5B30.002). Following incubation, the samples were washed with BSA stain buffer and stained with PE-goat anti-mouse IgG polyclonal to detect bound antibody on live SupT1 cells. After incubation, washing, and fixation, the samples were acquired on a 10 color FACSCanto II flow cytometer. Analysis was done using FlowJo and the PE median fluorescent intensity of live SupT1 cells is plotted in FIG. 3. As shown in FIG. 3, dose dependent binding of GP5B318 to GP5DB83-LH SupT1 cells. No binding was detected on CAR– SupT1 parental cells.

Figure 4:
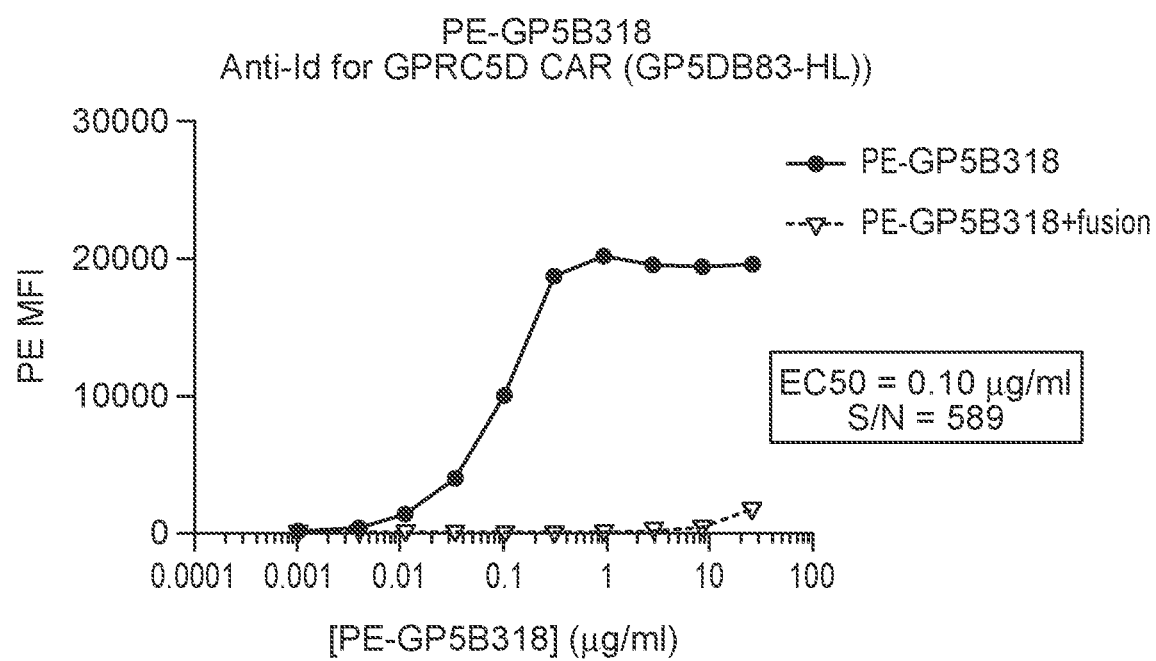
FIG. 4 shows a graphical representation of blocking the dose dependent binding of PE-P5B318 to GP5DB83-HL SupT1 cells with GPDB83-HL scFv-Fc fusion protein.

GP5B318 was conjugated to R-PE as described above and tested for binding to GP5DB83-HL SupT1 in the presence or absence of 10 μg/mL GP5DB83-scFv Fc fusion protein to assess the specificity of GP5B318 binding to GP5DB83-HL CAR and ensure CAR detection was not affected by PE labeling. GP5DB83-HL SupT1 cells were stained with near IR LIVE/DEAD fluorescent reactive dye in 50 mL tube on ice for 20 mins. After incubation, the cells were washed and resuspended in BSA stain buffer to 2×10$^6$ cells/mL. 100,000 cells/well were seeded in 96 well plate and incubated with increasing concentrations of PE-GP5B318 and 10 μg/mL GP5DB83-scFv Fc for 45 minutes on ice. After incubation, washing, and fixation, the samples were acquired on a 10 color FACSCanto II flow cytometer. Analysis was performed using FlowJo analysis software and the PE median fluorescent intensity of live SupT1 cells is plotted in FIG. 4. As shown in FIG. 4, dose dependent binding of PE-P5B318 to GP5DB83-HL SupT1 cells is specific to GP5DB83-HL CAR and can be blocked by 10 μg/mL GPDB83-HL scFv Fc.

TABLE 3

SEQUENCES
CDR and Framework Sequences
VH CDR and framework

| SEQ ID NO. | Region | Definition | Sequence Fragment | Residues | Length |
|---|---|---|---|---|---|
| 1 | HFR1 | Chothia | EVQLVQSGAEVKKPGESLKISCKGS----- | 1-25 | 25 |
| 1 | | AbM | EVQLVQSGAEVKKPGESLKISCKGS----- | 1-25 | 25 |
| 2 | | Kabat | EVQLVQSGAEVKKPGESLKISCKGSGYSFT | 1-30 | 30 |
| 3 | | Contact | EVQLVQSGAEVKKPGESLKISCKGSGYSF- | 1-29 | 29 |
| 4 | CDR-H1 | Chothia | GYSFTSY--- | 26-32 | 7 |
| 5 | | AbM | GYSFTSYWIG | 26-35 | 10 |
| 6 | | Kabat | -----SYWIG | 31-35 | 5 |
| 7 | | Contact | ----TSYWIG | 30-35 | 6 |
| 8 | HFR2 | Chothia | WIGWVRQMPGKGLEWMGII | 33-51 | 19 |
| 9 | | AbM | ---WVRQMPGKGLEWMG-- | 36-49 | 14 |
| 9 | | Kabat | ---WVRQMPGKGLEWMG-- | 36-49 | 14 |
| 10 | | Contact | ---WVRQMPGKGLE----- | 36-46 | 11 |
| 11 | CDR-H2 | Chothia | -----YPGDSD--------- | 52-57 | 6 |
| 12 | | AbM | ---IIYPGDSDTR------- | 50-59 | 10 |
| 13 | | Kabat | ---IIYPGDSDTRYSPSFQG | 50-66 | 17 |
| 14 | | Contact | WMGIIYPGDSDTR------- | 47-59 | 13 |
| 15 | HFR3 | Chothia | TRYSPSFQGQVTISADKSISTAYLQWSSLKASDTAMYYCAR | 58-98 | 41 |
| 16 | | AbM | --YSPSFQGQVTISADKSISTAYLQWSSLKASDTAMYYCAR | 60-98 | 39 |
| 17 | | Kabat | ---------QVTISADKSISTAYLQWSSLKASDTAMYYCAR | 67-98 | 32 |
| 18 | | Contact | --YSPSFQGQVTISADKSISTAYLQWSSLKASDTAMYYC-- | 60-96 | 37 |
| 19 | CDR-H3 | Chothia | --GWDYGTGEFDY | 99-109 | 11 |
| 19 | | AbM | --GWDYGTGEFDY | 99-109 | 11 |
| 19 | | Kabat | --GWDYGTGEFDY | 99-109 | 11 |
| 20 | | Contact | ARGWDYGTGEFD- | 97-108 | 12 |
| 21 | HFR4 | Chothia | -WGQGTLVTVSS | 110-120 | 11 |
| 21 | | AbM | -WGQGTLVTVSS | 110-120 | 11 |
| 21 | | Kabat | -WGQGTLVTVSS | 110-120 | 11 |
| 22 | | Contact | YWGQGTLVTVSS | 109-120 | 12 |

VL CDR and framework

| SEQ ID NO. | Region | Definition | Sequence Fragment | Residues | Length |
|---|---|---|---|---|---|
| 23 | LFR 1 | Chothia | EIVLTQSPGTLSLSPGERATLSC------ | 1-23 | 23 |
| 23 | | AbM | EIVLTQSPGTLSLSPGERATLSC------ | 1-23 | 23 |
| 23 | | Kabat | EIVLTQSPGTLSLSPGERATLSC------ | 1-23 | 23 |
| 24 | | Contact | EIVLTQSPGTLSLSPGERATLSCRASQSI | 1-29 | 29 |

VL CDR and framework

| SEQ ID NO. | Region | Definition | Sequence Fragment | Residues | Length |
|---|---|---|---|---|---|
| 25 | CDR-L1 | Chothia | RASQSIGNWLN-- | 24-34 | 11 |
| 25 | | AbM | RASQSIGNWLN-- | 24-34 | 11 |
| 25 | | Kabat | RASQSIGNWLN-- | 24-34 | 11 |
| 26 | | Contact | ------GNWLNWY | 30-36 | 7 |
| 27 | LFR2 | Chothia | WYQQKPGKAPKLLIY | 35-49 | 15 |
| 27 | | AbM | WYQQKPGKAPKLLIY | 35-49 | 15 |
| 27 | | Kabat | WYQQKPGKAPKLLIY | 35-49 | 15 |
| 28 | | Contact | --QQKPGKAPK---- | 37-45 | 9 |
| 29 | CDR-L2 | Chothia | YASSLQS | 50-56 | 7 |
| 29 | | AbM | ----YASSLQS | 50-56 | 7 |
| 29 | | Kabat | ----YASSLQS | 50-56 | 7 |
| 30 | | Contact | LLIYYASSLQ- | 46-55 | 10 |
| 31 | LFR3 | Chothia | -GVPSRFSGSGSGTDFTLTISSLQPEDFAVYYC | 57-88 | 32 |
| 31 | | AbM | -GVPSRFSGSGSGTDFTLTISSLQPEDFAVYYC | 57-88 | 32 |
| 31 | | Kabat | -GVPSRFSGSGSGTDFTLTISSLQPEDFAVYYC | 57-88 | 32 |
| 32 | | Contact | SGVPSRFSGSGSGTDFTLTISSLQPEDFAVYYC | 56-88 | 33 |
| 33 | CDR-L3 | Chothia | QQSLSFPIT | 89-97 | 9 |
| 33 | | AbM | QQSLSFPIT | 89-97 | 9 |
| 33 | | Kabat | QQSLSFPIT | 89-97 | 9 |
| 34 | | Contact | QQSLSFPI- | 89-96 | 8 |
| 35 | LFR4 | Chothia | -FGQGTKVEIK | 98-107 | 10 |
| 35 | | AbM | -FGQGTKVEIK | 98-107 | 10 |
| 35 | | Kabat | -FGQGTKVEIK | 98-107 | 10 |
| 36 | | Contact | TFGQGTKVEIK | 97-107 | 11 |

SEQ ID No. 37: Heavy Chain of GP5B318 with muIgG2a (amino acid)
EVQLVQSGAEVKKPGESLKISCKGSGYSFTSYWIGWVRQMPGKGLEWMGI
IYPGDSDTRYSPSFQGQVTISADKSISTAYLQWSSLKASDTAMYYCARGW
DYGTGEFDYWGQGTLVTVSSAKTTAPSVYPLAPVCGDTTGSSVTLGCLVK
GYFPEPVTLTWNSGSLSSGVHTFPAVLQSDLYTLSSSVTVTSSTWPSQSI
TCNVAHPASSTKVDKKIEPRGPTIKPCPPCKCPAPNLLGGPSVFIFPPKI
KDVLMISLSPIVTCVVVDVSEDDPDVQISWFVNNVEVHTAQTQTHREDYN
STLRVVSALPIQHQDWMSGKEFKCKVNNKDLPAPIERTISKPKGSVRAPQ
VYVLPPPEEEMTKKQVTLTCMVTDFMPEDIYVEWTNNGKTELNYKNTEPV
LDSDGSYFMYSKLRVEKKNWVERNSYSCSVVHEGLHNHHTTKSFSRTPGK SEQ ID No. 38: Heavy Chain of GP5B318 with muIgG2a (DNA)
GAAGTGCAGCTGGTGCAGAGCGGCGCGGAAGTGAAAAAACCGGGCGAAAG
CCTGAAAATTAGCTGCAAAGGCAGCGGCTATAGCTTTACCAGCTATTGGA
TTGGTTGGGTGCGCCAGATGCCGGGCAAAGGCCTGGAATGGATGGGCATT
ATTTATCCGGGTGATAGCGATACCCGTTATAGCCCGAGCTTTCAGGGCCA
GGTGACCATTAGCGCGGATAAAAGCATTAGCACCGCGTATCTGCAGTGGA
GCAGCCTGAAAGCGAGCGATACCGCGATGTATTATTGCGCGCGCGGCTGG
GACTATGGTACCGGCGAGTTCGACTATTGGGGCCAGGGCACCCTGGTGAC
CGTGAGCAGCGCCAAAACAACAGCACCAAGTGTCTATCCACTGGCCCCTG
TGTGTGGAGATACAACTGGCTCCTCGGTGACTCTAGGATGCCTGGTCAAG
GGTTATTTCCCTGAGCCAGTGACCTTGACCTGGAACTCTGGATCCCTGTC
CAGTGGTGTGCACACCTTCCCAGCTGTCCTGCAGTCTGACCTCTACACCC
TCAGCAGCTCAGTGACTGTAACCTCGAGCACCTGGCCCAGCCAGTCCATC
ACCTGCAATGTGGCCCACCCGGCAAGCAGCACCAAGGTGGACAAGAAAAT
TGAGCCCAGAGGGCCCACAATCAAGCCCTGTCCTCCATGCAAATGCCCAG
CACCTAACCTCTTGGGTGGACCATCCGTCTTCATCTTCCCTCCAAAGATC
AAGGATGTACTCATGATCTCCCTGAGCCCCATAGTCACATGTGTGGTGGT
GGATGTGAGCGAGGATGACCCAGATGTCCAGATCAGCTGGTTTGTGAACA
ACGTGGAAGTACACAGCTCAGACACAAACCCATAGAGAGGATTACAAC
AGTACTCTCCGGGTGGTCAGTGCCCTCCCCATCCAGCACCAGGACTGGAT
GAGTGGCAAGGAGTTCAAATGCAAGGTCAACAACAAAGACCTCCCAGCGC
CCATCGAGAGAACCATCTCAAAACCCAAAGGGTCAGTAAGAGCTCCACAG
GTATATGTCTTGCCTCCACCAGAAGAAGAGATGACTAAGAAACAGGTCAC
TCTGACCTGCATGGTCACAGACTTCATGCCTGAAGACATTTACGTGGAGT
GGACCAACAACGGGAAAACAGAGCTAAACTACAAGAACACTGAACCAGTC
CTGGACTCTGATGGTTCTTACTTCATGTACAGCAAGCTGAGAGTGGAAAA
GAAGAACTGGGTGGAAAGAAATAGCTACTCCTGTTCAGTGGTCCACGAGG
GTCTGCACAATCACCACACGACTAAGAGCTTCTCCCGGACTCCGGGTAAA SEQ ID No. 39: Light Chain of GP5B318 with muKappa (amino acid)
EIVLTQSPGTLSLSPGERATLSCRASQSIGNWLNWYQQKPGKAPKLLIYY
ASSLQSGVPSRFSGSGSGTDFTLTISSLQPEDFAVYYCQQSLSFPITFGQ

GTKVEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC

SEQ ID No. 40: Light Chain of GP5B318 with muKappa (DNA)
GAAATTGTGCTGACCCAGAGCCCGGGCACCCTGAGCCTGAGCCCGGGCGA

ACGCGCGACCCTGAGCTGCCGCGCGAGCCAGAGCATCGGTAACTGGCTGA

ACTGGTATCAGCAGAAACCGGGCAAAGCGCCGAAACTGCTGATTTATTAC

GCGAGCAGCCTGCAGAGCGGCGTGCCGAGCCGCTTTAGCGGCAGCGGCAG

CGGCACCGATTTTACCCTGACCATTAGCAGCCTGCAGCCGGAAGATTTTG

CGGTGTATTATTGCCAGCAGTCCCTTTCCTTTCCGATTACATTTGGCCAG

GGCACCAAAGTGGAAATTAAACGGGCTGATGCTGCACCGACTGTGTCCAT

CTTCCCACCATCCAGTGAGCAGTTAACATCTGGAGGTGCCTCAGTCGTGT

GCTTCTTGAACAACTTCTACCCCAAAGACATCAATGTCAAGTGGAAGATT

GATGGCAGTGAACGACAAAATGGCGTCCTGAACAGTTGGACTGATCAGGA

CAGCAAAGACAGCACCTACAGCATGAGCAGCACCCTCACGTTGACCAAGG

ACGAGTATGAACGACATAACAGCTATACCTGTGAGGCCACTCACAAGACA

TCAACTTCACCCATTGTCAAGAGCTTCAACAGGAATGAGTGT

SEQ ID No. 41: GP5B83 N23T/N30S VH
QLQLQESGPGLVKPSETLSLTCTVSGGSLSSSSYWWGWTRQPPGRGLEWI

GTMYYSGNIYYNPSLQSRATISVDTSKNQFSLKLSSVTAADTAVYYCARH

VGYSYGRRFWYFDLWGRGTLVTVSS

SEQ ID No. 42: GP5B83 VL
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIK

SEQ ID NO: 43 - CAR 1 (GP5B83-HL)
QLQLQESGPGLVKPSETLSLTCTVSGGSLSSSSYWWGWTRQPPGRGLEWI

GTMYYSGNIYYNPSLQSRATISVDTSKNQFSLKLSSVTAADTAVYYCARH

VGYSYGRRFWYFDLWGRGTLVTVSSGGSEGKSSGSGSESKSTGGSEIVLT

QSPATLSLSPGERATLSCRASQSVSSYLAWYQQKPGQAPRLLIYDASNRA

TGIPARFSGSGSGTDFTLTISSLEPEDFAVYYCQQRSNWPPTFGQGTKVE

IKTSTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCS

CRFPEEEEGGCELRVKFSRSADAPAYKQGQNQLYNELNLGRREEYDVLDK

RRGRDPEMGGKPRRKNPQEGLYNELQKDKMAEAYSEIGMKGERRRGKGHD

GLYQGLSTATKDTYDALHMQALPPR

SEQ ID NO: 44 - CAR 2 (GP5B83-LH)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIKGGSEGKSSGSGSESKSTGGSQLQLQESGPGLVKPSETLSLTCT

VSGGSLSSSSYWWGWTRQPPGRGLEWIGTMYYSGNIYYNPSLQSRATISV

DTSKNQFSLKLSSVTAADTAVYYCARHVGYSYGRRFWYFDLWGRGTLVTV

SSTSTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCS

CRFPEEEEGGCELRVKFSRSADAPAYKQGQNQLYNELNLGRREEYDVLDK

RRGRDPEMGGKPRRKNPQEGLYNELQKDKMAEAYSEIGMKGERRRGKGHD

GLYQGLSTATKDTYDALHMQALPPR

SEQ ID No. 45: Heavy Chain Variable Domain of GP5B318 (amino acid)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARGW

DYGTGEFDYWGQGTLVTVSS

SEQ ID No. 46: Light Chain Variable Domain of GP5B318 (amino acid)
EIVLTQSPGTLSLSPGERATLSCRASQSIGNWLNWYQQKPGKAPKLLIYY

ASSLQSGVPSRFSGSGSGTDFTLTISSLQPEDFAVYYCQQSLSFPITFGQ

GTKVEIK

SEQ ID NO: 47 - human GPRC5D sequence (amino acid)
MYKDCIESTGDYFLLCDAEGPWGIILESLAILGIVVTILLLLAFLFLMRK

IQDCSQWNVLPTQLLFLLSVLGLFGLAFAFIIELNQQTAPVRYFLFGVLF

ALCFSCLLAHASNLVKLVRGCVSFSWTTILCIAIGCSLLQIIIATEYVTL

IMTRGMMFVNMTPCQLNVDFVVLLVYVLFLMALTFFVSKATFCGPCENWK

QHGRLIFITVLFSIIIWVVWISMLLRGNPQFQRQPQWDDPVVCIALVTNA

WVFLLLYIVPELCILYRSCRQECPLQGNACPVTAYQHSFQVENQELSRAR

DSDGAEEDVALTSYGTPIQPQTVDPTQECFIPQAKLSPQQDAGGV

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An anti-idiotype antibody or an antigen-binding portion thereof that specifically binds GP5B83, wherein the anti-idiotype antibody or antigen-binding portion thereof comprises:
   a heavy chain complementarity determining region 1 (CDR1) comprising the amino acid sequence of SEQ ID NO: 4, a heavy chain CDR2 comprising the amino acid sequence of SEQ ID NO: 11, and a heavy chain CDR3 comprising the amino acid sequence of SEQ ID NO: 19, and a light chain CDR1 comprising the amino acid sequence of SEQ ID NO: 25, a light chain CDR2 comprising the amino acid sequence of SEQ ID NO: 29, and a light chain CDR3 comprising the amino acid sequence of SEQ ID NO: 33; or
   a heavy chain CDR1 comprising the amino acid sequence of SEQ ID NO: 5, a heavy chain CDR2 comprising the amino acid sequence of SEQ ID NO: 12, and a heavy chain CDR3 comprising the amino acid sequence of SEQ ID NO: 19, and a light chain CDR1 comprising the amino acid sequence of SEQ ID NO: 25, a light chain CDR2 comprising the amino acid sequence of SEQ ID NO: 29, and a light chain CDR3 comprising the amino acid sequence of SEQ ID NO: 33; or
   a heavy chain CDR1 comprising the amino acid sequence of SEQ ID NO: 6, a heavy chain CDR2 comprising the amino acid sequence of SEQ ID NO: 13, and a heavy chain CDR3 comprising the amino acid sequence of SEQ ID NO: 19, and a light chain CDR1 comprising the amino acid sequence of SEQ ID NO: 25, a light chain CDR2 comprising the amino acid sequence of SEQ ID NO: 29, and a light chain CDR3 comprising the amino acid sequence of SEQ ID NO: 33; or
   a heavy chain CDR1 comprising the amino acid sequence of SEQ ID NO: 7, a heavy chain CDR2 comprising the amino acid sequence of SEQ ID NO: 14, and a heavy chain CDR3 comprising the amino acid sequence of SEQ ID NO: 20, and a light chain CDR1 comprising the amino acid sequence of SEQ ID NO: 26, a light chain CDR2 comprising the amino acid sequence of SEQ ID NO: 30, and a light chain CDR3 comprising the amino acid sequence of SEQ ID NO: 34.

2. The anti-idiotype antibody or antigen-binding portion thereof of claim 1, wherein the VH domain comprises at least 90% sequence identity to SEQ ID NO:45 and the VL domain comprises at least 90% sequence identity to SEQ ID NO:46.

3. The anti-idiotype antibody or antigen-binding portion thereof of claim 1, wherein the anti-idiotype antibody or antigen-binding portion thereof comprises a heavy chain comprising at least 90% sequence identity to SEQ ID NO:37 and comprises a light chain comprising at least 90% sequence identity to SEQ ID NO:39.

4. The anti-idiotype antibody or antigen-binding portion thereof of claim 1, wherein the VH domain comprises SEQ ID NO:45 and the VL domain comprises sequence of SEQ ID NO:46.

5. The anti-idiotype antibody or antigen-binding portion thereof of claim 1, wherein the anti-idiotype antibody or antigen-binding portion thereof comprises a heavy chain comprising SEQ ID NO:37 and a light chain comprising SEQ ID NO:39.

6. The anti-idiotype antibody or antigen-binding portion thereof of claim 1, wherein the antigen binding portion thereof is selected from a Fab, F(ab')2, or scFv.

7. The anti-idiotype antibody or antigen-binding portion thereof of claim 1, wherein the antibody is a monoclonal antibody.

8. The anti-idiotype antibody or antigen-binding portion thereof of claim 1, wherein the antibody is a chimeric antibody.

9. The anti-idiotype antibody or antigen-binding portion thereof of claim 8, wherein the antibody comprises a murine IgG2a framework.

10. The anti-idiotype antibody or antigen-binding portion thereof of claim 1, wherein the anti-idiotype antibody or antigen-binding portion thereof binds a target antibody that comprises GP5B83, wherein the target antibody or antigen-binding portion thereof comprises a VH domain comprising SEQ ID NO: 41 and a VL domain comprising SEQ ID NO: 42.

11. The anti-idiotype antibody or antigen-binding portion thereof of claim 1, wherein GP5B83 is within the antigen-binding domain of the extracellular portion of a chimeric antigen receptor (CAR).

12. The anti-idiotype antibody or antigen-binding portion thereof of claim 11 wherein GP5B83 is an scFv and the anti-idiotype antibody or antigen-binding portion thereof specifically binds an epitope in the scFv of the CAR.

13. The anti-idiotype antibody or antigen-binding portion thereof of claim 11, wherein GP5B83 specifically binds GPRC5d.

14. The anti-idiotype antibody or antigen-binding portion thereof of claim 11, wherein the antibody or antigen-binding portion thereof does not cross-react to other GPRC5d antibodies or other GPRC5d binding CARs.

15. The anti-idiotype antibody or antigen-binding portion thereof of claim 11, wherein the CAR amino acid sequence is selected from the group consisting of SEQ ID NO: 43-44.

16. A kit for detecting GP5B83 in a biologic sample comprising: (a) the anti-idiotype antibody or antigen-binding portion thereof of claim 1; and (b) instructions for detecting the anti-idiotype antibody or antigen-binding portion thereof.

17. A nucleic acid encoding the heavy chain and the light chain of the anti-idiotype antibody or antigen-binding portion thereof of claim 1.

18. A nucleic acid encoding the heavy chain and the light chain of an anti-idiotype antibody or an antigen-binding portion thereof that specifically binds GP5B83, wherein said nucleic acid comprises the nucleotide sequence of SEQ ID NO: 38 and the nucleotide sequence of SEQ ID NO: 40.

19. A vector comprising the nucleic acid of claims 18.

20. The vector of claim 19, wherein the vector is an expression vector.

21. A host cell comprising the vector of claim 20.

22. The host cell of claim 21, wherein the cell is a mammalian cell.

23. A method of producing an anti-idiotype antibody or antigen-binding portion thereof that specifically binds GPSB83, said method comprising culturing the host cell of claim 21 under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture.

24. A method for detecting expression of a chimeric antigen receptor (CAR) comprising GP5B83 in a biologic sample comprising: (a) providing a biological sample; (b) contacting the biological sample with the anti-idiotype antibody or antigen-binding portion thereof of claim 1; and (c) detecting the anti-idiotype antibody or antigen-binding portion thereof, and thereby detecting the expression of the CAR.

25. A method for detecting GP5B83 in a biologic sample comprising: (a) providing a biological sample; (b) contacting the biological sample with the anti-idiotype antibody or antigen-binding portion thereof of claim 1; and (c) detecting the anti-idiotype antibody or antigen-binding portion thereof.

26. The method according to claim 25, wherein the antibody comprises a detectable label.

27. The method according to claim 25, wherein the method further comprises contacting the anti-idiotype antibody or antigen-binding portion thereof with a detectable label before detecting the anti-idiotype antibody or antigen-binding portion thereof.

28. The method according to claim 25, wherein the biological sample is blood, serum or urine.

29. A method of purifying GP5B83 from a sample comprising: (a) providing a biological sample comprising GP5B83; (b) contacting the biological sample with the anti-idiotype antibody or antigen-binding portion thereof of claim 1; and (c) capturing the anti-idiotype antibody or antigen-binding portion thereof, and thereby purifying GP5B83.

30. A method of selecting CAR-T cells from a cell population comprising: (a) providing a biological sample comprising CAR-T cells; (b) contacting the biological sample with the anti-idiotype antibody or antigen-binding portion thereof of claim 1; and (c) capturing the anti-idiotype antibody or antigen-binding portion thereof, and thereby selecting CAR-T cells.

* * * * *